US006800745B1

(12) United States Patent
Selsted

(10) Patent No.: US 6,800,745 B1
(45) Date of Patent: Oct. 5, 2004

(54) INDOLICIDIN ANALOGS AND METHODS OF USING SAME

(75) Inventor: Michael E. Selsted, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/417,265

(22) Filed: Oct. 12, 1999

Related U.S. Application Data

(62) Division of application No. 09/076,227, filed on May 12, 1998, now Pat. No. 6,303,575.

(51) Int. Cl.[7] .................... A61K 38/04; A61K 39/00; C07K 16/00; A23C 3/00

(52) U.S. Cl. .................... 536/23.1; 514/12; 514/13; 514/14; 514/15; 424/274.1; 424/326

(58) Field of Search .................... 514/14, 12, 15, 514/44; 530/324, 327; 426/326, 335, 332; 435/69.1, 69.6, 91.1, 91.2, 91.3, 91.4, 91.41, 91.42, 471, 490; 536/22.1, 23.1, 23.5

(56) References Cited

U.S. PATENT DOCUMENTS

| 5,166,321 A | 11/1992 | Lai et al. ............... 530/324 |
| 5,324,716 A | 6/1994 | Selsted et al. ........... 514/14 |
| 5,428,015 A | 6/1995 | Kurono et al. ........... 514/12 |
| 5,432,261 A | 7/1995 | Kurono et al. ........... 530/326 |
| 5,547,939 A | 8/1996 | Selsted .................. 514/14 |
| 6,037,456 A | * 3/2000 | Garger et al. ........... 530/412 |
| 6,180,604 B1 | 1/2001 | Fraser et al. ........... 514/12 |
| 6,294,372 B1 | * 9/2001 | Burian et al. ......... 435/252.33 |

FOREIGN PATENT DOCUMENTS

| CA | WO9708199 | * 3/1997 |
| CA | WO9807745 | * 2/1998 |
| EP | 0 286 239 A1 | 10/1988 |
| WO | WO 97/08199 | 3/1997 |
| WO | 98/07745 | * 2/1998 |

OTHER PUBLICATIONS

Del Sal et al. (1992) "cDNA cloning of the neutrophil bacterial peptide indilicidin" Biochem. Biophys. Res. Comm. vol. 187, 467–472.*
Lim et al., "Synthesis and biological characterization of indolicidin analogues," J. Biochem. Mol. Biol. 30(3):229–233 (1997).
Uchida et al., "Antibacterial activity of the mammalian host defense peptide, indolicidin, and its fragments," Peptide Chem. . 229–232 (1996).
Ahmad et al., "Liposomal entrapment of the neutrophil–derived peptide indolicidin endows it with in vivo antifungal activity", Biochem. Biophys. Acta, 1237:109–114(1995).

Del Sal et al., "cDNA Cloning Of The Neutrophil Bactericidal Peptide Indolicidin", Biochem. Biophys. Res. Comm., 187(1):467–472 (1992).
Falla and Hancock, "Improved Activity of a Synthetic Indolicidin Analog", Antimicrob. Agents Chemother., 41(4): 771–775 (1997).
Gregoriadis, Gregory (ed.), Liposome Technology: vol. 1—Preparation of Liposomes, CRC Press, Inc. (1984).
Hultmark et al., "Insect immunity. Attacins, a family of antibacterial proteins from Hyalophora cecropia", EMBO J., 2(4):571–576 (1983).
Ikehara et al., "Synthesis of a gene for human growth hormone and its expression in Escherichia coli", Proc. Natl. Acad. Sci. USA, 81:5956–5960 (1984).
Lehrer et al., "Ultrasensitive assays for endogenous antimicrobial polypeptides", J. Immuno. Meth., 137:167–173 (1991).
Rees et al. (eds.), Protein Engineering: A Practical Approach, IRL Press (1992).
Setlow, Jane K. (ed.), Genetic Engineering: Principles and Methods vol. 15, Plenum Press (1993).
Subbalakshmi et al., "Requirements for antibacterial and hemolytic activities in the bovine neutrophil derived 13–residue peptide indolicidin", FEBS Letters, 395:48–52 (1996).
Van Abel et al., "Synthesis and characterization of indolicidin, a tryptophan–rich antimicrobial peptide from bovine neutrophils", Int. J. Peptide Protein Res., 45:401–409 (1995).
Wade et al., "All–D amino acid–containing channel–forming antibiotic peptides", Proc. Natl. Acad. Sci. USA, 87:4761–4765 (1990).

* cited by examiner

Primary Examiner—Karen Cochrane Carlson
(74) Attorney, Agent, or Firm—McDermott Will & Emery LLP

(57) ABSTRACT

The present invention relates to analogs of indolicidin, which is a naturally occurring peptide having the amino acid sequence Ile-Leu-Pro-Trp-Lys-Trp-Pro-Trp-Trp-Pro-Trp-Arg-Arg-NH$_2$ ("Indol 1–13;" SEQ ID NO: 1). The indolicidin analogs of the invention include, for example, analogs such as Indol 2–13 (SEQ ID NO: 2) and Indol 3–13 (SEQ ID NO: 3), which are truncated at the amino terminus by one and two amino acids, respectively, as compared to Indol 1–13 (SEQ ID NO: 1); analogs in which at least one Trp residue in an amino terminal truncated indolicidin analog is replaced by a Phe residue ("Indol/F") analogs"); indolicidin analogs comprising, at the carboxy terminus, a homoserine residue; and fusion polypeptides comprising an indolicidin analog. In addition, the invention provides nucleic acid molecules encoding the indolicidin analogs of the invention or precursors of such analogs. The invention also relates to methods of using the indolicidin analogs to reduce or inhibit microbial growth or survival by contacting an environment capable of sustaining microbial growth with the indolicidin analog.

23 Claims, 7 Drawing Sheets

```
G GAA TTC GAC GAC GAC GAC AAA ATG ATC CTG CCG TGG AAA TGG CCG
c ctt aag ctg ctg ctg ctg ttt tac tag gac ggc acc ttt acc ggc
Eco RI   Asp Asp Asp Asp Lys Met Ile Leu Pro Trp Lys Trp Pro
                             ⇑   ↑
TGG TGG CCG TGG CGT CGT ATG GCT CGT ATC GCT ATG ATC CTG CCG
acc acc ggc acc gca gca tac cga gca tag cga tac tag gac ggc
Trp Trp Pro Trp Arg Arg Met Ala Arg Ile Ala Met Ile Leu Pro
                            ↑                   ↑
TGG AAA TGG CCG TGG TGG CCG TGG CGT CGT ATG GCT CGT ATC GCT
acc ttt acc ggc acc acc ggc acc gca gca tac cga gca tag cga
Trp Lys Trp Pro Trp Trp Pro Trp Arg Arg Met Ala Arg Ile Ala
                                            ↑
ATG ATC CTG CCG TGG AAA TGG CCG TGG TGG CCG TGG CGT CGT ATG
tac tag gac ggc acc ttt acc ggc acc acc ggc acc gca gca tac
Met Ile Leu Pro Trp Lys Trp Pro Trp Trp Pro Trp Arg Arg Met
    ↑                                                       ↑
GCT CGT ATC GCT ATG TAA TAA GTC GAC CGG
cga gca tag cga tac att att cag ctg gcc
Ala Arg Ile Ala Met Stp Stp    Sal I
```

INDOLICIDIN ANALOGS AND METHODS OF USING SAME

This application is a divisional of application Ser. No. 09/076,227, filed May 12, 1998, now U.S. Pat. No. 6,303,575.

BACKGROUND OF THE INVENTION

1. Field of the Invention

The present invention relates generally to antimicrobial agents and, more specifically, to indolicidin analogs and methods of using the analogs to reduce or inhibit microbial growth or survival.

2. Background Information

Infections by microorganisms, including bacteria, viruses and fungi, are a major cause of human morbidity and mortality. Although anyone can be a victim of such infection, the sick and elderly are particularly susceptible. For example, hospitalized patients frequently acquire secondary infections due to a combination of their weakened condition and the prevalence of microorganisms in a hospital setting. Such opportunistic infections result in increased suffering of the patient, increased length of hospitalization and, consequently, increased costs to the patient and the health care system. Similarly, the elderly, particularly those living in nursing homes or retirement communities, are susceptible to infections because of their close living arrangement and the impaired responsiveness of their immune systems.

Numerous drugs are available for treating infections by certain microorganisms. In particular, various bacterial infections have been amenable to treatment by antibiotics. However, the prolonged use of antibiotics since their discovery has resulted in the selection of bacteria that are relatively resistant to these drugs. Furthermore, few if any drugs are effective against microorganisms such as viruses. As a result, continuing efforts are being made to identify new and effective agents for treating infections by a variety of microorganisms.

The identification of naturally occurring compounds that act as antimicrobial agents has provided novel and effective drugs. Many organisms protect themselves by producing natural products that are toxic to other organisms. Frogs, for example, produce a class of peptides, magainins, that are highly toxic if ingested, thus providing a defense mechanism for the frog against potential predators. Magainins have been purified and shown to have antimicrobial activity, thus providing a natural product useful for reducing or inhibiting microbial infections.

Natural products useful as antimicrobial agents also have been purified from mammalian organisms, including humans. For example, the defensins are a class of peptides that have been purified from mammalian neutrophils and demonstrated to have antimicrobial activity. Similarly, indolicidin is a peptide that has been isolated from bovine neutrophils and has antimicrobial activity, including activity against viruses, bacteria, fungi and protozoan parasites. Thus, naturally occurring compounds provide a source of drugs that are potentially useful for treating microbial infections.

Upon identifying naturally occurring peptides useful as antimicrobial agents, efforts began to chemically modify the peptides to obtain analogs having improved properties. Such efforts have resulted, for example, in the identification of indolicidin analogs which, when administered to an individual, have increased selectivity against the infecting microorganisms as compared to the individual's own cells. Thus, the availability of naturally occurring antimicrobial agents has provided new drugs for treating microbial infections and has provided a starting material to identify analogs of the naturally occurring molecule that have desirable characteristics.

Although such natural products and their analogs have provided new agents for treating microbial infections, it is well known that microorganisms can become resistant to drugs. Thus, a need exists to identify agents that effectively reduce or inhibit the growth or survival of microorganisms. The present invention satisfies this need and provides additional advantages.

SUMMARY OF THE INVENTION

The present invention relates to analogs of indolicidin, which is a naturally occurring peptide having the amino acid sequence Ile-Leu-Pro-Trp-Lys-Trp-Pro-Trp-Trp-Pro-Trp-Arg-Arg-CONH$_2$ ("Indol 1–13; " SEQ ID NO: 1). As disclosed herein, indolicidin analogs of the invention have the structure:

X1-X2-X3-X4-X5-X6-P-X6-X6-P-X6-X7-X7-X8, wherein X1 is Ile, Leu, Val, Ala, Gly or absent; X2 is Ile, Leu, Val, Ala, Gly or absent; X3 is Pro or absent; X4 is Trp, Phe or absent; X5 is Arg, Lys or absent; X6 is Trp or Phe; X7 is Arg, Lys or absent; and X8 is homoserine, Met, Met-X9-Met or absent, wherein X9 is at least one amino acid; provided that if X1 is present, either X8 is homoserine, Met or Met-X9-Met, wherein X9 is at least one amino acid, or both occurrences of X7 are absent; and further provided that if X2 is absent, X1 is absent; if X3 is absent, X1 and X2 are absent; if X4 is absent, X1, X2 and X3 are absent; and if X5 is absent, X1, k2, X3 and X4 are absent. For example, the invention provides amino terminal truncated indolicidin analogs, including Indol 2–13 (SEQ ID NO: 2), Indol 3–13 (SEQ ID NO: 3), Indol 4–13 (SEQ ID NO: 4) and Indol 5–13 (SEQ ID NO: 5), each of which has broad spectrum antimicrobial activity.

The invention also provides indolicidin analogs, wherein at least one of the Trp residues in an amino terminal truncated indolicidin analog is replaced by a Phe residue ("Indol/F" analogs). For example, the invention provides Indol 2–13/F (SEQ ID NO: 11), in which each of the Trp residues in Indol 2–13 (SEQ ID NO: 2) is replaced with a Phe residue.

Amino terminal truncated indolicidin analogs lacking a carboxy terminal amide also are provided. In addition, the invention provides indolicidin analogs comprising, at the carboxy terminus, a homoserine ("Hse") residue ("Indol-Hse"), such analogs having antimicrobial activity. For example, the invention provides Indol-Hse analogs such as H$_2$N-Ile-Leu-Pro-Trp-Lys-Trp-Pro-Trp-Trp-Pro-Trp-Arg-Arg-Hse (SEQ ID NO: 24; "Indol(1–13)-Hse"), Indol (2–13)-Hse and the like, and similarly provides Indol/F-Hse analogs, including Indol 1–13/F-Hse. Furthermore, the invention provides nucleic acid molecules encoding the indolicidin analogs of the invention or precursors of such analogs.

The ability of an Indol-Hse or Indol/F-Hse analog to exhibit antimicrobial activity provides a means for expressing poly-indolicidin analog polypeptides in vitro or in vivo, wherein each indolicidin analog in the polypeptide is separated by a Met residue or by the sequence Met-X9-Met, such that treatment of the polypeptide with cyanogen bromide results in the production Indol-Hse or Indol/F-Hse analogs.

For example, Met-X9-Met can be Met-Gly-Ser-Glu-Met (SEQ ID NO: 20) or Met-Ala-Arg-Ile-Ala-Met (SEQ ID NO: 21) or the like. Expression, for example, of one mole of Indol, 1–13/F-(M-G-S-E-M)-Indol 1–13/F-M (SEQ ID NO: 22), which consists of two unamidated Indol 1–13/F peptides separated by the sequence Met-Gly-Ser-Glu-Met (SEQ ID NO: 20) and including a carboxy terminal Met, followed by treatment with cyanogen bromide results in the production of two moles of Indol 1–13/F-Hse (SEQ ID NO: 23). The expression of such poly-indolicidin analog polypeptides provides a convenient means to produce substantial amounts of indolicidin analog peptides from a host organism, including a microorganism, because the polypeptide form of the analogs does not have substantial antimicrobial activity. In addition, the invention provides fusion polypeptides comprising an indolicidin analog and a peptide of interest, which can be useful, for example, for facilitating purification of an expressed indolicidin analog.

The invention also relates to methods of using an indolicidin analog to reduce or inhibit microbial growth or survival in an environment capable of sustaining microbial growth or survival by contacting the environment with the indolicidin analog. As such, the invention provides methods of reducing or inhibiting microbial growth or survival on a solid surface, for example, surgical instruments, hospital surfaces, and the like. In addition, methods of the invention are useful for reducing or inhibiting microbial growth or survival in an individual, particularly a mammal such as a human. Thus, the invention provides methods of treating an individual suffering from a pathology caused, at least in part, by microbial infection, by administering an indolicidin analog to the individual, thereby reducing the severity of the pathologic condition.

BRIEF DESCRIPTION OF THE DRAWINGS

FIG. 6 shows the nucleotide sequence (SEQ ID NO:38) encoding poly-(Indol(1–13)-Met-Ala-Arg-Ile-Ala-Met)$_3$, which encodes three copies of Indol 1–13, each separated by Met-Ala-Arg-Ile-Ala-Met (SEQ ID NO: 21). The coding (sense) strand is shown in capital letters, the antisense strand is shown in lower case letters, and the encoded amino acid sequence (SEQ ID NO:39) is shown using the three letter code ("Stp" indicates STOP codon). Eco RI and Sal I restriction endonuclease sites are indicated. The enterokinase recognition site is singly underlined, with the double arrow indicating the cleavage site. The single arrows denote cyanogen bromide cleavage sites. Dotted underlined tetranucleotide sequences correspond to overlaps in oligonucleotides used for ligation. Double underlined sequences denote primers used for PCR amplification (see Example I.B).

DETAILED DESCRIPTION OF THE INVENTION

The present invention provides isolated indolicidin analogs having the general structure: X1-X2-X3-X4-X5-X6-P-X6-X6-P-X6-X7-X7-X8, wherein X1 is Ile, Leu, Val, Ala, Gly or absent; X2 is Ile, Leu, Val, Ala, Gly or absent; X3 is Pro or absent; X4 is Trp, Phe or absent; X5 is Arg, Lys or absent; X6 is Trp or Phe; X7 is Arg, Lys or absent; and X8 is homoserine or absent; provided that if X1 is present, either X8 is homoserine (Hse), Met or Met-X9-Met, wherein X9 is at least one amino acid, or both occurrences of X7 are absent; and further provided that if X2 is absent, X1 is absent; if X3 is absent, X1 and X2 are absent; if X4 is absent, X1, X2 and X3 are absent; and if X5 is absent, X1, X2, X3 and X4 are absent. In particular, the invention provides amino terminal truncated indolicidin analogs, including analogs wherein one or more Trp residues in the analog is replaced by Phe (see Tables 1 and 2); to indolicidin analogs, including full length indolicidin analogs, containing at the carboxy terminus a homoserine (Hse) residue, a Met residue or the amino acid sequence Met-X9-Met, for example, Met-Gly-Ser-Glu-Met (SEQ ID NO: 20), Met-Ala-Arg-Ile-Ala-Met (SEQ ID NO: 21) or the like; and to fusion polypeptides comprising such an indolicidin analog.

Indolicidin is a naturally occurring peptide having the amino acid sequence Ile-Leu-Pro-Trp-Lys-Trp-Pro-Trp-Trp-Pro-Trp-Arg-Arg-CONH$_2$ ("Indol 1–13; " SEQ ID NO: 1). Indolicidin (SEQ ID NO: 1) was named based on its tryptophan-rich nature and its microbicidal properties (see U.S. Pat. No. 5,324,716, issued Jun. 28, 1994, which is incorporated herein by reference).

Indolicidin analogs having the general structure H$_2$N-I-L-P-W-K-W-P-W-W-W-P-W-X (SEQ ID NO: 23), where X designates one or two independently selected amino acids, have been described (see U.S. Pat. No. 5,534,939, issued Aug. 20, 1996). Such indolicidin analogs, like indolicidin (SEQ ID NO: 1), are tryptophan-rich peptide and are characterized, in part, by having improved selectivity as compared to indolicidin (SEQ ID NO: 1). Additional indolicidin analogs also have been described (International Publ. No. WO 97/08199, published Mar. 6, 1997). These previously described indolicidin analogs are distinguishable from those of the present invention in that the previously described analogs either contain an amino acid residue as represented by X1 in -X1-X2-X3-X4-X5-X6-P-X6-X6-P-X6-X7-X7-X8 or lack Hse, Met or Met-X9-Met at the carboxy terminus.

Figure 1:
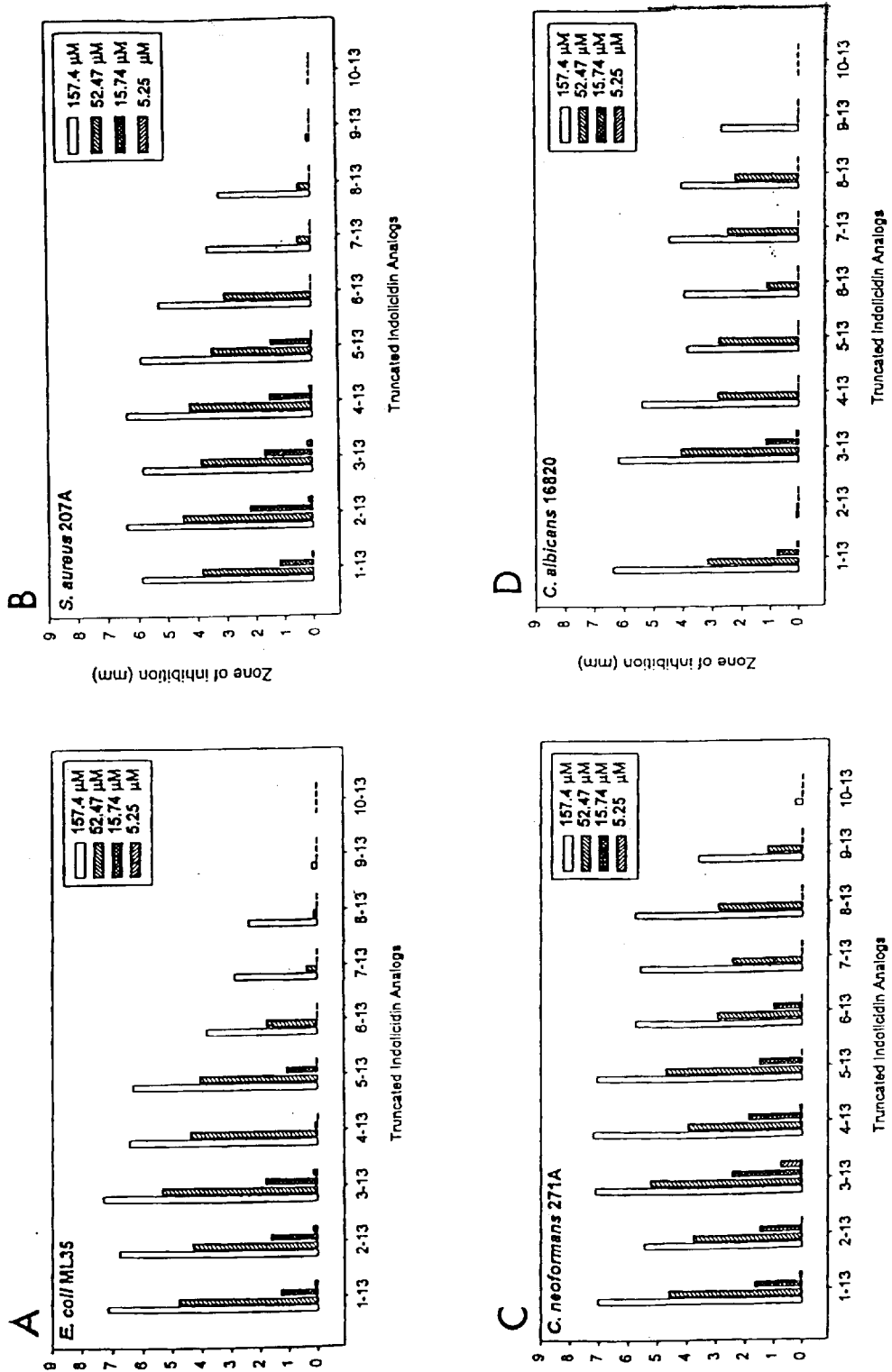
FIGS. 1A to 1D compare the antimicrobial activity of synthetic Indol 1–13 (SEQ ID NO: 1) and various amino terminal truncated indolicidin analogs, as indicated, using an agar diffusion assay. Antimicrobial activity was examined against *Escherichia coli* (FIG. 1A), *Staphylococccus aureus* (FIG. 1B), *Cryptococcus neoformans* (FIG. 1C) or *Candida albicans* (FIG. 1D). Peptides were added at concentrations ranging from 5.25 µM to 157.4 µM and zones of inhibition were measured (millimeters, "mm").
Figure 2:
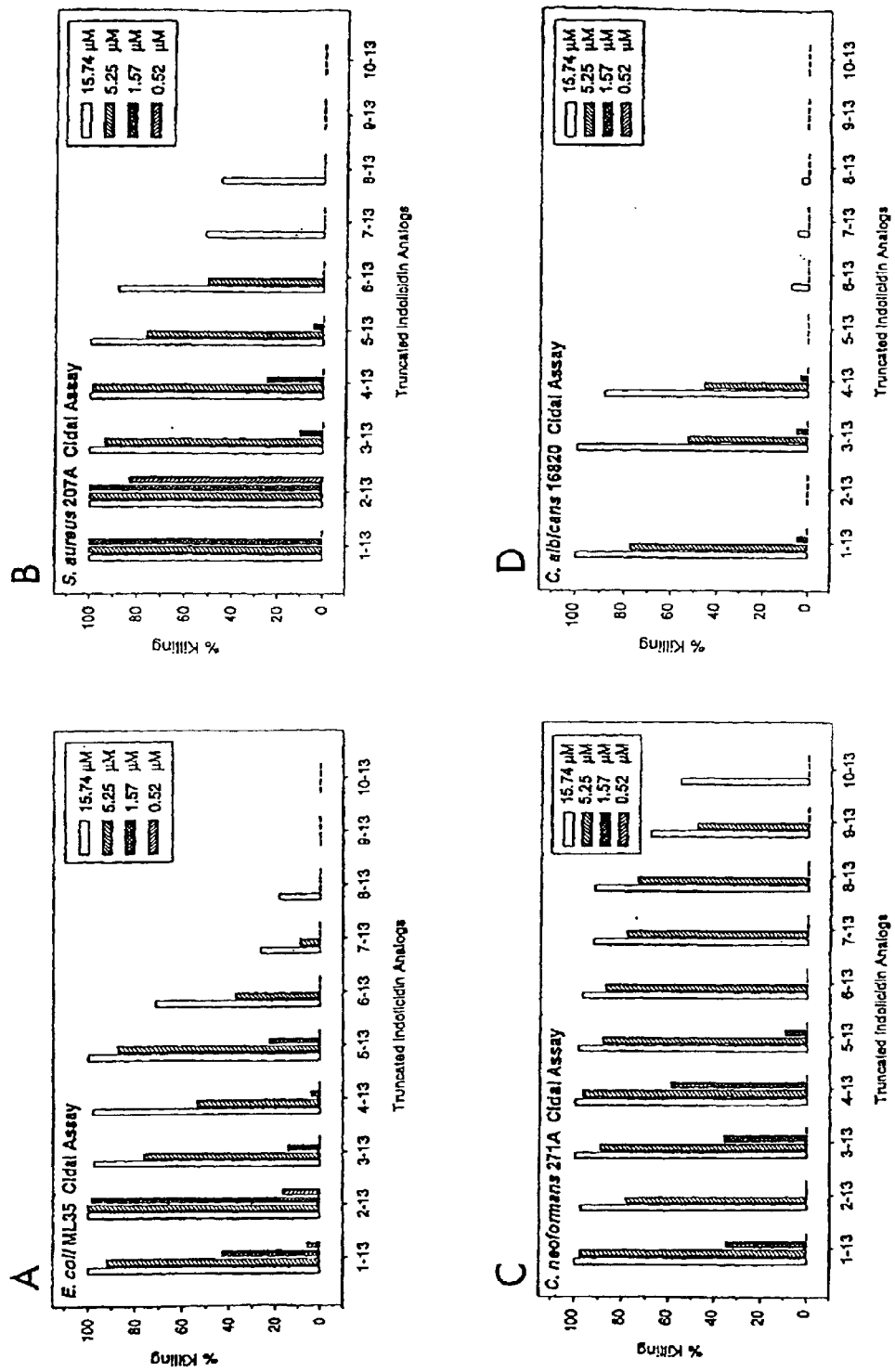
FIGS. 2A to 2D compare the antimicrobial activity of Indol 1–13 (SEQ ID NO: 1) and various amino terminal truncated indolicidin analogs, as indicated, using a suspension assay. Antimicrobial activity was examined against *Escherichia coli* (FIG. 2A), *Staphylococccus aureus* (FIG. 2B), *Cryptococcus neoformans* (FIG. 2C) or *Candida albicans* (FIG. 2D). Peptides were added at concentrations ranging from 0.52 µM to 15.74 µM and % killing was determined.
Figure 3:
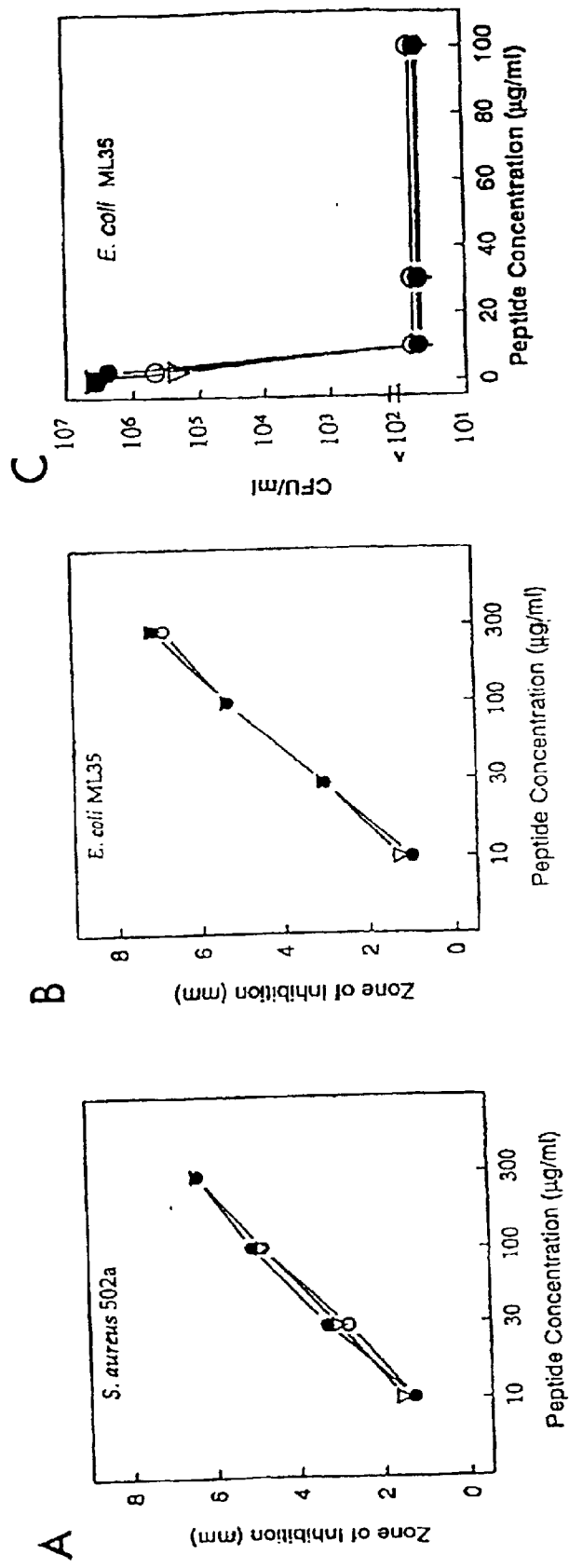
FIGS. 3A to 3C compare the antimicrobial activity of Indol 1–13 (SEQ ID NO: 1; open circles) with the homoserine acid lactone (closed circles) and the lactone Indol-Hse analogs produced after cyanogen bromide cleavage of Indol(1–13)-Met-Gly-Ser-Glu (SEQ ID NO: 35) using an agar diffusion assay (FIGS. 3A and 3B) or a bactericidal assay (FIG. 3C). Peptides were examined at the indicated concentrations against *S. aureus* (FIG. 3A) or *E. coli* (FIGS. 3B and 3C). Zones of inhibition (mm) were determined for the agar diffusion assays and colony forming units (CFU)/ml were determined for the bactericidal assays.
Figure 4:
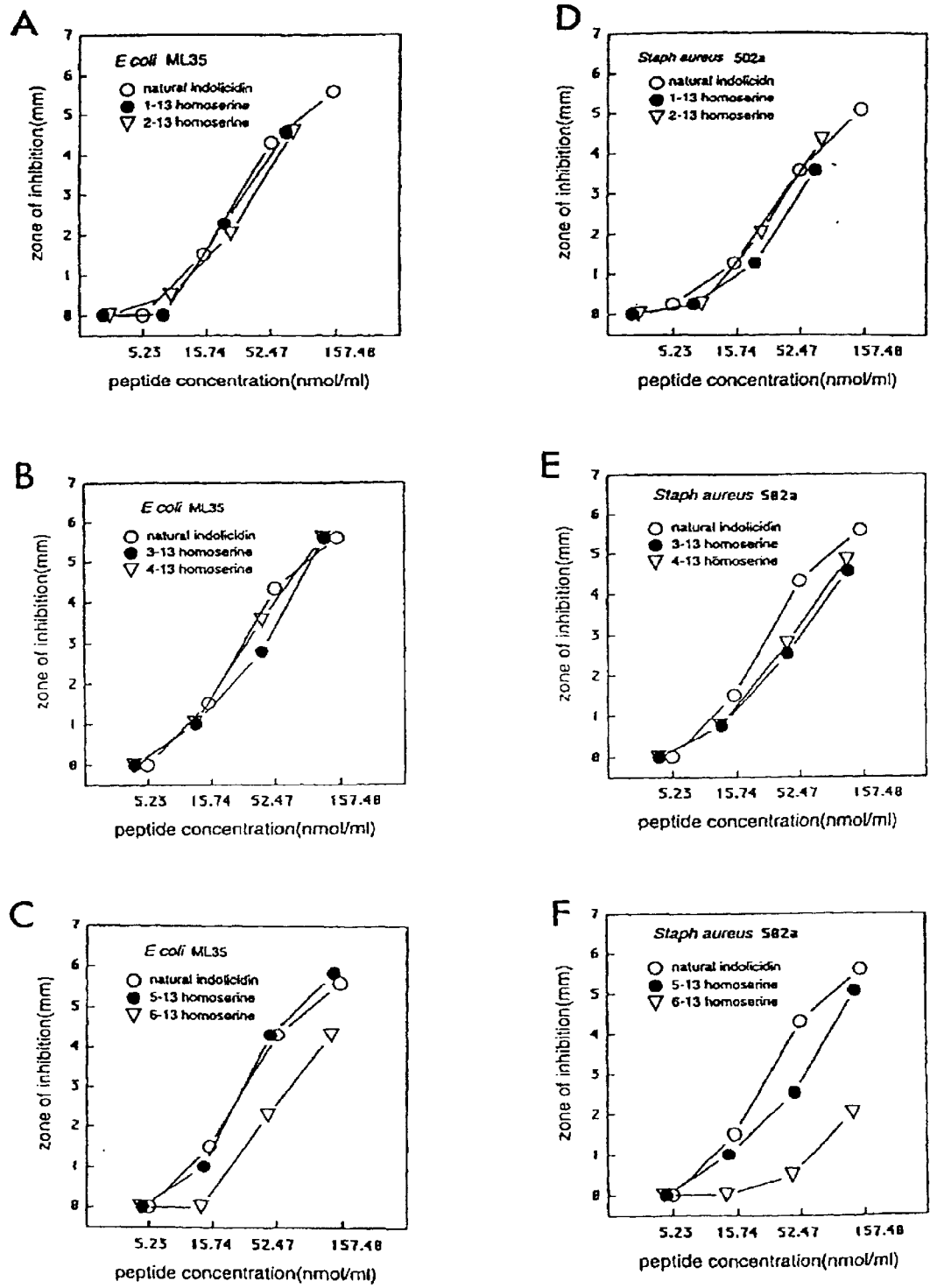
FIGS. 4A to 4F compare the antimicrobial activities of Indol 1–13 (SEQ ID NO: 1) and various amino terminal truncated Indol-Hse analogs, as indicated, using an agar diffusion assay. Antibacterial activity was determined against *E. coli* (FIG. 4A to 4C) or *S. aureus* (FIGS. 4D to 4F). Zones of inhibition were determined for peptide concentrations ranging from 5.25 µM to 157.4 µM (nmol/ml).

As disclosed herein, an indolicidin analog of the invention can be an amino terminal truncated indolicidin analog such as Indol 2–13 (SEQ ID NO: 2), Indol 3–13 (SEQ ID NO: 3), Indol 4–13 (SEQ ID NO: 4) or Indol 5–13 (SEQ ID NO: 5; see Table 1), each of which exhibits antimicrobial activity (see, for example, FIGS. 1 and 2). In addition, an indolicidin analog can be an amino truncated indolicidin analog where, in addition, one or more Trp residues is replaced by a Phe residue (see Table 2). For example, substitution of all of the Trp residues in Indol 2–13 (SEQ ID NO: 2) with Phe results in the indolicidin analog Indol 2–13/F (SEQ ID NO: 11; see Table 2), which exhibits antimicrobial activity (see FIG. 5).

An indolicidin analog of the invention is based on the general structure of indolicidin (SEQ ID NO: 1), except that various defined amino acid deletions, substitutions or additions are made with respect to indolicidin. As used herein, the term "amino acid" is used in its broadest sense to mean the naturally occurring amino acids as well as non-naturally occurring amino acids, including amino acid analogs. Thus, reference herein to an amino acid includes, for example, naturally occurring proteogenic (L)-amino acids, as well as (D)-amino acids, chemically modified amino acids such as amino acid analogs, naturally occurring non-proteogenic amino acids such as norleucine, and chemically synthesized compounds having properties known in the art to be characteristic of an amino acid. As used herein, the term "proteogenic" indicates that the amino acid can be incorporated into a protein in a cell through a metabolic pathway.

The amino acid residue at any position in an indolicidin analog having the structure shown as X1-X2-X3-X4-X5-X6-P-X6-X6-P-X6-X7-X7-X8 can be independently selected. As used herein, the term "independently selected" indicates that the choice of an amino acid residue at any one position in an indolicidin analog does not depend on or influence the selection of amino acid residue at any other position in the analog. Thus, the selection of a Trp residue for X6 shown at position 6 of X1-X2-X3-X4-X5-X6-P-X6-X6-P-X6-X7-X7-X8 does not influence whether, for example, the amino acid present at the X6 shown in position 8 is a Trp residue or a Phe residue.

Reference to an amino acid position in an indolicidin analog is made herein with respect to the amino acid position in naturally occurring indolicidin (SEQ ID NO: 1). As such, the positions are referred to as positions 1 through 13, starting with the Ile residue in SEQ ID NO: 1 (position 1) and ending with the carboxy terminal arginine (position 13). As a result, although Leu is the first amino acid in Indol 2–13 (SEQ ID NO: 2), this Leu residue is referred to as being located at position 2 because this is the location of the corresponding Leu in SEQ ID NO: 1. It follows that SEQ ID NO: 2 is referred to as Indol 2–13 because it begins with an amino acid corresponding to the second amino acid (Leu) of indolicidin (Indol 1–13; SEQ ID NO: 1; see Table 1).

An indolicidin analog containing at least one substitution of a Phe residue for a Trp residue is referred to herein generally as an "Indol(Trp/Phe)" or an "Indol/F" analog. Since the exemplified indolicidin analogs contain a global substitution of Phe for every Trp in the peptide, no specific designation for the position of the substitution is made in naming the exemplified analogs. Thus, the designation "Indol 2–13/F" indicates an indolicidin analog that lacks one amino terminal amino acid as compared to naturally occurring indolicidin (SEQ ID NO: 1) and contains a Phe substitution for every Trp otherwise present in indolicidin. However, the present invention encompasses indolicidin analogs containing as few as one Phe-for-Trp substitution, for example, at position 4 or 6 or 8 or 9 or 11. Where fewer than all of the Trp residues in an analog are replaced with a Phe, the nomenclature for the analog includes a number indicating the position of the substitution. For example, "Indol 2–13/6F" indicates an indolicidin analog that lacks one amino terminal amino acid as compared to naturally occurring indolicidin (SEQ ID NO: 1) and contains a substitution of Phe for Trp only at position 6; similarly, "Indol 2–13/6,11F" contains Phe for Trp substitutions at positions 6 and 11.

As disclosed herein, amino terminal truncation of naturally occurring indolicidin results in the production of indolicidin analogs having antimicrobial activity (see Example II). In view of this disclosure, the skilled artisan will recognize that various amino acid substitutions can be made in certain positions without destroying the antimicrobial activity of the derived analog. Thus, whereas Indol 1–13 (SEQ ID NO: 1) contains an Ile residue at position 1, the skilled artisan, knowing that this Ile can be deleted without destroying antimicrobial activity, would recognize that Ile also can be conservatively substituted with an amino acid such as Leu, Val, Ala or Gly without destroying the antimicrobial activity of the indolicidin analog. Similarly, conservative amino acid substitutions are permissible for the Leu at position 2. In addition, the substitution of an Arg residue for Lys at position 5 is permitted, as indicated by disclosure that the substitution of a Lys for Arg-12 or for Arg-13 results in indolicidin analogs having antimicrobial activity (see U.S. Pat. No. 5,534,939, supra, 1996).

Furthermore, since indolicidin analogs that lack a carboxy terminal Arg residue or that contain a Lys substitution for one or both of the carboxy terminal Arg residues have antimicrobial activity (U.S. Pat. No. 5,547,939, supra, 1996), such deletions or conservative amino acid substitutions are permissible in the indolicidin analogs of the present invention, provided that, when one Arg residue is deleted or when one or both Arg residues are substituted for with a Lys, at least X1 is absent X1-X2-X3-X4-X5-X6-P-X6-X6-P-X6-X7-X7-X8 or a carboxy terminal Met, Met-X9-Met or Hse is present (see Table 3). Such indolicidin analogs further can be Indol/F analogs, as desired, and are referred to, for example, as "Indol 2–12/F" or "Indol 2–12/F/12K" or "Indol 1–13/F-Hse" or the like, within the constraints of the nomenclature set forth above. As disclosed herein, such amino and carboxy terminal truncated indolicidin analogs have antimicrobial activity. For example, Indol 3–12 (SEQ ID NO: 27), Indol 4–12 (SEQ ID NO: 28), Indol 5–12 (SEQ ID NO: 29) and Indol 6–12 (SEQ ID NO: 30) have substantial antimicrobial activity against fungi such as Cryptococcus.

An indolicidin analog of the invention can be expressed from an encoding nucleic acid molecule in vitro or in vivo in a host cell or can be chemically synthesized. With respect to expressing the analogs, nucleic acid sequences encoding the various indolicidin analogs of the invention can be prepared based, for example, on the disclosure of the indolicidin nucleic acid sequence (Del Sal et al., *Biochem. Biophys. Res. Comm.* 187:467–472 (1992), which is incorporated herein by reference) and on knowledge in the art of the codons for the amino acids comprising the various disclosed indolicidin analogs. Such nucleic acids encoding the indolicidin analogs can be cloned into an appropriate vector, particularly an expression vector, and the encoded analog can be expressed using an in vitro transcription/translation reaction. In addition, such nucleic acid sequences can be used to construct a synthetic gene encoding a poly-indolicidin analog polypeptide, which can cloned into an expression vector and expressed in vivo in a bacterial, insect or mammalian host cells (see Example I.B). An advantage of expressing a poly-indolicidin analog polypeptide in vivo is that large amounts can be prepared using, for example, commercial fermentation methods, since the polypeptide form of the analogs does not appear to have substantial antimicrobial activity, then the polypeptide can be cleaved to produce active indolicidin analogs.

An indolicidin analog also can be chemically synthesized using well known methods (see, for example, van Abel et al., *Internatl. J. Pept. Prot. Res.* 45:401–409 (1995), which is incorporated herein by reference; see, also, Example I.A). An advantage of using chemical synthesis to prepare an indolicidin analog is that (D)-amino acids can be substituted for (L)-amino acids, if desired. The incorporation of one or more (D)-amino acids into an indolicidin analog can confer desirable characteristics on the peptide, for example, increased stability in vitro or, particularly, in vivo, since endogenous proteases generally are ineffective against peptides comprising (D)-amino acids. Naturally occurring antimicrobial peptides that have been chemically synthesized to contain (D)-amino acids maintain their antimicrobial activity (Wade et al., *Proc. Natl. Acad. Sci. USA* 87:4761–4765 (1990), which is incorporated herein by reference).

Indolicidin analogs were synthesized using an automated peptide synthesizer such as an Eppendorf Synostat (Madison Wis.) or a Milligen 9050 (Milford Mass.; Example I.A), although manual methods of solution peptide synthesis also can be used. Indolicidin analogs were synthesized on an Fmoc-(5-(4-Fmoc-aminomethyl-3,5-dimethoxyphenoxy) valeric acid-polyethylene glycol-polystyrene (Fmoc-PAL-PEG-PS) resin (Fmoc is 9-fluorenylmethyloxycarbonyl; Milligen; see Example I.A). However, the skilled artisan would know that other resins, amino acid derivatives and methods of modifying amino acid reactive groups or the amino terminus, for example, by acetylation, or the carboxy terminus can be used to obtain a desired indolicidin analog (see, for example, *Protein Engineering: A practical approach* (IRL Press 1992); Bodanszky, *Principles of Peptide Synthesis* (Springer-Verlag 1984), each of which is incorporated herein by reference). The synthesized indolicidin analogs were purified by reversed phase HPLC and characterized by fast atom bombardment mass spectroscopy, acid-urea gel electrophoresis and analytical HPLC (see Example I.A) or can be purified and characterized using other routine methods of peptide purification and analysis.

Selective modification of a reactive group can impart desirable characteristics to an indolicidin analog. The choice of including such a modification is determined, in part, by the characteristics required of the peptide. Such modifications can result, for example, in indolicidin analogs having greater antimicrobial selectivity or potency than naturally occurring indolicidin. As used herein, the term "antimicrobial selectivity" refers to the relative amount of antimicrobial activity of an analog against a microorganism as compared to its activity against the environment to which it is administered, particularly its activity against normal cells in a treated individual. For example, an indolicidin analog that is characterized by having antimicrobial activity that is equivalent to indolicidin, but having decreased hemolytic activity as compared to indolicidin, is considered to have greater antimicrobial selectivity than indolicidin.

Indolicidin analogs having greater antimicrobial selectivity than naturally occurring indolicidin have been described. For example, indolicidin analogs truncated at the carboxy terminus or having one or more lysine substitutions for the carboxy terminal arginines in naturally occurring indolicidin have antimicrobial activity similar to indolicidin, but have decreased hemolytic activity (U.S. Pat. No. 5,547,939, supra, 1996). Also, indolicidin analogs in which all of the Trp residues were substituted with Phe, but not analogs having Ala for Pro substitutions, had greater antimicrobial selectivity than indolicidin (Subbalakshmi et al., *FEBS Lett.* 395:48–52 (1996), which is incorporated herein by reference). Indolicidin analogs containing various other amino acid substitutions or modifications, for example, carboxymethylation of the carboxy terminal also have desirable properties (Fall and Hancock, *Antimicr. Agents Chemother.* 41:771–775 (1997), which is incorporated herein by reference; see, also, WO 97/08199, supra, 1997). None of the previously described indolicidin analogs, however, are amino terminal truncated analogs of indolicidin. The antimicrobial selectivity of an indolicidin analog can be determined using the methods disclosed herein (see Example II) or using routine methods such as those described in the above cited references (see, also, Selsted, M. E. Investigational approaches for studying the structures and biological functions of myeloid antimicrobial peptides. In: *Genetic Engineering: Principles and Methods* Vol. 15 (Setlow, ed.; Plenum Press, New York 1993); see pages 131–147, which are incorporated herein by reference).

The indolicidin analogs of the invention have broad spectrum antimicrobial activity (see FIGS. 1 to 5; Example II). As used herein, the term "broad spectrum," when used in reference to the antimicrobial activity of an indolicidin analog, refers to the ability of the analog to reduce or inhibit the survival or proliferative ability of various prokaryotic and eukaryotic microorganisms. For example, indolicidin analogs of the invention can exhibit antimicrobial activity against protozoans such as *Giardia lamblia*, Chlamydia sp. and Acanthamoeba sp.; viruses, particularly enveloped viruses such as HIV-1; yeast and fungi such as Cryptococcus and Candida; various genera of gram negative and gram positive bacteria, including Escherichia, Salmonella and Staphylococcus; and helminths such as liver flukes. Antimicrobial activity can occur through microbicidal inhibition, which refers to the ability of an indolicidin analog to reduce or inhibit the survival of a microorganism by killing or irreversibly damaging it, or through microbistatic inhibition, which refers to the ability of an indolicidin analog to reduce or inhibit the growth or proliferative ability of a target microorganism without necessarily killing it.

As disclosed herein, various amino terminal truncated indolicidin analogs (Tables 1 and 2); amino terminal and carboxy terminal truncated indolicidin analogs (Table 3); and indolicidin analogs having a carboxy terminal Hse residue, Indol(1–13)-Hse (see FIG. 4), were prepared and examined for antimicrobial activity. Indol 2–13 (SEQ ID NO: 2), Indol 3–13 (SEQ ID NO: 3), Indol 4–13 (SEQ ID NO: 4), Indol 5–13 (SEQ ID NO: 5) and Indol(1–13)-Hse, for example, demonstrated similar antimicrobial selectivity, specificity and potency as Indol 1–13, as did various Indol/F analogs, including Indol/F-Hse analogs, and analogs truncated from both the amino terminus and carboxy terminus (see Example II).

The determination that Indol-Hse and Indol/F-Hse analogs maintain antimicrobial activity is significant because an Hse group remains at the carboxy terminus of a peptide following cyanogen bromide cleavage of the peptide at a Met residue. Since indolicidin analogs of the invention do not contain internal Met residues, the analogs are not cleaved upon exposure to cyanogen bromide. The Hse at the carboxy terminus of a peptide typically exists as an equilibrium state between the lactone and carboxylate forms and, as disclosed herein, both forms of the Hse analogs exhibit substantial antimicrobial activity (see FIG. 3). If desired, an Indol-Hse analog can be amidated at the carboxy terminus.

The disclosed ability of an Indol-Hse analog to maintain antimicrobial activity provides a means to produce substantial quantities of the analog by expressing a poly-(Indol-Met)$_N$ polypeptide, where "N" is the number of times the Indol-Met sequence is repeated, and cleaving the polypeptide with cyanogen bromide to produce N Indol-Hse analog peptides (see Example I.B; see, also, FIG. 6). In particular, such a method can be performed in vivo in a host cell because a poly-(Indol-Met)$_N$ polypeptide does not exhibit substantial antimicrobial activity. Such a method is performed, for example, by synthesizing a nucleic acid sequence encoding the Indol portion of the analog and a carboxy terminal Met; ligating the nucleic acid sequences, such that the encoded peptides are maintained in the same reading frame, to produce a synthetic gene comprising a concatemer having N repeats of the Indol-Met coding sequence; cloning the synthetic gene into an expression vector such that the encoded poly-(Indol-Met)$_N$ is expressed from the promoter in the vector; transforming a host cell with the vector; expressing the encoded poly-(Indol-Met)$_N$ polypeptide; and cleaving the polypeptide with cyanogen bromide to produce N Indol-Hse analogs. Thus, the invention provides Indol-Hse and Indol/F-Hse analogs, including Indol(1–13)-Hse and Indol 1–13/F-Hse analogs, which have antimicrobial activity (see FIG. 7).

Purification of the expressed poly-(Indol-Met)$_N$ polypeptide is facilitated by further linking the synthetic gene to a nucleic acid sequence encoding a peptide that is capable of being bound by a molecule. Such a peptide can be a ligand or a receptor, which can be specifically bound by an appropriate receptor or ligand, respectively; or a peptide that is specifically bound by an antibody. In addition, a peptide linked to a poly-(Indol-Met)$_N$ polypeptide can be any peptide of interest, for example, a peptide such as alkaline phosphatase or green fluorescent protein, which provide a means to detect the presence of the fusion polypeptide.

For facilitating purification of a poly-indolicidin analog polypeptide, the linked peptide can be, for example, maltose binding protein, which binds maltose or a maltose containing oligosaccharide such as amylose; glutathione-S-transferase (GST), which binds glutathione; His-6, which is bound by a metal ion such as nickel ion or cobalt ion; the FLAG epitope, which is bound by anti-FLAG antibody; or any other peptide for which a specific antibody is available. If desired, the molecule, for example, glutathione, that binds the peptide (GST), can be attached to a solid support such as a chromatography matrix and an expressed poly-(Indol-Met)$_N$-GST fusion polypeptide can be purified from contaminating host cell proteins by passage over the matrix. If desired, the fusion polypeptide can be eluted from the matrix and treated with cyanogen bromide; or the fusion polypeptide, while attached to the matrix, can be exposed to cyanogen bromide, thereby releasing only the Indol-Hse analogs. Thus, the invention provides fusion polypeptides comprising an indolicidin analog linked to a peptide of interest.

The invention also provides nucleic acid molecules encoding the indolicidin analogs of the invention. Thus, the invention provides nucleic acid molecules encoding amino terminal truncated indolicidin analogs, including amino terminal truncated Indol and Indol/F analogs, as well as nucleic acid molecules encoding indolicidin analog precursors that contain at least a carboxy terminal methionine residue, such precursors resulting in the formation of Indol-Hse or Indol/F-Hse analogs of the invention. A nucleic acid molecule of the invention also can encode a poly-indolicidin analog polypeptide or a fusion polypeptide comprising an indolicidin analog, as disclosed herein.

The skilled artisan will know that the nucleotide sequences of the nucleic acid molecules of the invention can be determined based on the amino acid sequence of the indolicidin analog and knowledge of the codons encoding the various amino acids. Such codons can be selected using computer assisted methods. One or another degenerate codon, for example, one of the six codons encoding Arg or one of the six codons encoding Leu or the like, can be selected as desired, for example, to prevent (or include) the insertion of a restriction endonuclease site in the indolicidin analog coding sequence. The nucleic acid molecules of the invention are useful, for example, to produce indolicidin analogs in vitro using an appropriate transcription/translation system or in vivo using an appropriate expression system. The nucleic acid molecules of the invention can be polydeoxyribonucleotide sequences (DNA) or polyribonucleotide sequences (RNA), as desired, and can contain linkers, adapters or the like to facilitate cloning or concatemerization in the appropriate frame.

An indolicidin analog having antimicrobial activity can be applied to an environment capable of sustaining the survival or growth of a microorganism or to an environment at risk of supporting such survival or growth, thus providing a means for reducing or inhibiting microbial growth or survival. Accordingly, the invention relates to methods of using an indolicidin analog to reduce or inhibit microbial growth by contacting an environment capable of sustaining microbial growth or survival with the indolicidin analog.

As used herein, reference to "an environment capable of sustaining survival or growth of a microorganism" means a gaseous, liquid or solid material, including a living organism, in or upon which a microorganism can live or propagate. In view of the broad range of environments that allow the survival or growth of microorganisms as diverse, for example, as viruses, bacteria and fungi, and further in view of the disclosed effectiveness of the claimed indolicidin analogs against a broad spectrum of such microorganisms, the range of such environments that can be treated using a method of the invention necessarily is broad and includes, for example, a tissue or bodily fluid of an organism such as a human; a liquid such as water or an aqueous solution, for example, contact lens solution; a food such as a food crop, a food product or a food extract; an object such as the surface of an instrument used, for example, to prepare food or to perform surgery; and a gas such as that used for anesthetization in preparation for surgery.

A method of the invention encompasses administering to the environment an effective amount of an indolicidin analog such that the analog can contact a microorganism in the environment, thereby reducing or inhibiting the ability of the microorganism to grow or survive. The indolicidin analogs can be used in a variety of procedures for reducing or inhibiting the survival or growth of microorganisms, including the microbicidal inhibition of survival of a microorganism as well as the microbistatic inhibition of growth. As such, an indolicidin analog can be used, for example, as a therapeutic agent, a food preservative, a disinfectant or a medicament.

An indolicidin analog can be used as a therapeutic agent for treating a patient suffering from a bacterial, viral, fungal or other infection due to a microorganism susceptible to the antimicrobial activity of the analog. Thus, the invention provides methods of treating an individual suffering from a pathology caused, at least in part, by microbial infection, by administering an indolicidin analog to the individual under conditions that allow the analog to contact the infecting microorganisms, thereby reducing or inhibiting the survival or growth of the microorganism and alleviating the severity of the infection.

For use as a therapeutic agent, the indolicidin analog can be formulated with a pharmaceutically acceptable carrier to produce a pharmaceutical composition, which can be administered to the individual, which can be a human or other mammal. A pharmaceutically acceptable carrier can be, for example, water, sodium phosphate buffer, phosphate buffered saline, normal saline or Ringer's solution or other physiologically buffered saline, or other solvent or vehicle such as a glycol, glycerol, an oil such as olive oil or an injectable organic ester.

A pharmaceutically acceptable carrier can contain physiologically acceptable compounds that act, for example, to stabilize or increase the absorption of the indolicidin analog. Such physiologically acceptable compounds include, for example, carbohydrates such as glucose, sucrose or dextrans; antioxidants such as ascorbic acid or glutathione; chelating agents such as EDTA, which disrupts microbial membranes; divalent metal ions such as calcium or magnesium; low molecular weight proteins; or other stabilizers or excipients. One skilled in the art would know that the choice of a pharmaceutically acceptable carrier, including a physiologically acceptable compound, depends, for example, on the route of administration of the composition.

A pharmaceutical composition containing an indolicidin analog can be administered to an individual by various routes, including by intravenous, subcutaneous, intramuscular, intrathecal or intraperitoneal injection; orally, as an aerosol spray; or by intubation. If desired, the indolicidin analog can be incorporated into a liposome, a non-liposome lipid complex, or other polymer matrix, which further can have incorporated therein, for example, a second drug useful for treating the individual. Use of indolicidin incorporated into liposomes, for example, has been demonstrated to have antifungal activity in vivo (Ahmad et al., *Biochim. Biophys. Acta* 1237:109–114 (1995), which is incorporated herein by reference). Liposomes, which consist of phospholipids or other lipids, are nontoxic, physiologically acceptable and metabolizable carriers that are relatively simple to make and administer (Gregoriadis, *Liposome Technology*, Vol. 1 (CRC Press, Boca Raton Fla., 1984), which is incorporated herein by reference). The skilled artisan will select a particular route and method of administration based, for example, on the location of a microorganism in a subject, the particular characteristics of the microorganism, and the specific indolicidin analog that is administered.

Food and food products also can be treated with indolicidin analogs for the purpose of preserving the food or eliminating or preventing infection by microorganisms. For example, shellfish and poultry products routinely harbor enteric pathogenic microorganisms. The growth or survival of such microorganisms can be reduced or inhibited by contacting the product with an indolicidin analog. Food crops such as fruits, vegetables and grains can be treated with an indolicidin analog in order to reduce or inhibit post-harvest spoilage caused by microorganisms, for example, by administering the analog topically using an aerosolized form of the analog. In addition, transgenic plants or animals useful in the food industry can be produced by introducing a nucleic acid molecule encoding an indolicidin analog of the invention into the germline cells of such organisms. Methods for producing transgenic plants and animals are well known and routine in the art.

An indolicidin analog also can be used as a disinfectant to reduce or inhibit the survival or growth of microorganisms on an object, in a solution or in a gas. An indolicidin analog can be used to treat essentially any object or solution that can sustain microbial growth, where the survival or growth of the microorganisms is undesirable. In particular, an object or solution that comes into contact with a mammal such as a human, for example, baby wipes, diapers, band-aids, towelettes, make-up products and eyewash and contact lens solutions can be treated with an indolicidin analog. In such methods, the indolicidin analog can be applied topically to the object or can be added to the solution or can be in an aerosolized form in a gas.

In order to exhibit antimicrobial activity in an environment, an effective amount of an indolicidin analog is administered to the environment. As used herein, the term "effective amount" refers to the amount of an indolicidin analog that reduces or inhibits the survival or growth of a microorganism in an environment. In particular, an effective amount of an indolicidin analog produces only minimal effects against the environment, although the level of an acceptable deleterious effect is weighed against the benefit caused by the antimicrobial effect.

An indolicidin analog can be administered to a subject such as a human systemically at a dose ranging from 1 to 100 mg/kg body weight, for example, at a dose of about 10 to 80 mg/kg, particularly about 10 to 50 mg/kg, and the indolicidin analog can be incorporated in liposomes, if desired. In addition, an indolicidin analog can be administered topically to an environment, which can be a human subject, or can be placed in a solution, at a concentration of about 0.1 to 10 mg/ml, for example, at a concentration of about 0.5 to 5 mg/ml. Although indolicidin analogs generally are effective in such amounts, an effective amount for administration to a particular environment will depend, in part, on the environment. For example, when administered to a mammal such as a human, an indolicidin analog, in addition to having antimicrobial activity, can have hemolytic activity as a side effect. The skilled artisan will recognize that the level of such side effects must be considered in prescribing a treatment and must be monitored during the treatment period, and will adjust the amount of the analog that is administered accordingly. An effective amount also will vary depending, for example, on the characteristics of the target microorganism, the extent of prior infection or growth and the specific indolicidin analog administered. In addition, an effective amount depends on the form in which the indolicidin analog is administered. For example, incorporation of indolicidin into liposomes allowed administration of a higher amount than "free" indolicidin, without producing unacceptable side effects, such that fungal infection in mice could be cured (Ahmad et al., supra, 1995).

The following examples are intended to illustrate but not limit the present invention.

EXAMPLE I

Preparation and Characterization of Indolicidin Analogs

This example provides methods for chemically synthesizing indolicidin analogs and for expressing indolicidin analogs in a host cell.

A. Chemical Synthesis of Indol and Indol/F Analogs:

The peptide chain of indolicidin and various indolicidin analogs were assembled on an Fmoc-PAL-PEG-PS resin at 0.2 mmol scale on a Millipore 9050 Plus continuous-flow peptide synthesizer. The resin was swollen for 30 min in DMF before starting the synthesis. Fmoc-chemistry was utilized throughout.

Fmoc-cleavage was performed with 2% DBU-2% piperidine/DMF solution for 1 to 5 min. The following protecting groups were used: Arg(Pbf), Lys(tBoc), Trp (tBoc), Glu(OtBu), Ser(tBu), Cys(Trt). All amino acids were coupled by BOP/HOBt/NMM activation, using 5 min preactivation, 60 min coupling time, and 3-fold molar excess amino acid in each coupling reaction. Coupling of Ile, Leu, Trp(6) and Trp(9) were repeated (double coupled) for 40 min. After the last coupling, the Fmoc-group was cleaved from the peptide and the peptidyl-resin was washed with DCM and ethanol, then dried for 24 hr in vacuo.

For cleavage and deprotection, the peptidyl-resin was swollen in DCM in a manual reaction vessel, excess DCM was removed by filtration, and the resin was cooled to 0° C. Protecting groups were removed and the peptide was cleaved from the resin with Reagent-K (TFA-phenol-water-thioanisole-1,2-ethanedithiol; 82.5:5:5:5:2.5) using a ratio of 1.5 ml reagent K per gram of peptidyl-resin. The reaction vessel was shaken for 4 hr, then the resin was filtered, washed with fresh Reagent-K (1 ml/g resin), followed by DCM (3×10 ml/g resin) and, finally, 50% acetic acid/water (3×10 ml/g resin). The combined filtrates were placed in a separatory funnel and the aqueous phase was extracted twice more with DCM. The aqueous peptide solution was diluted with distilled water to a 10% final acetic acid concentration then freeze-dried. The lyophilization was repeated with the 5% acetic acid/water solution of the peptide. The crude product was isolated as a white fluffy powder.

The crude synthetic peptide was dissolved in 5% acetic acid/water (0.5 mg/ml peptide concentration) and subjected to RP-HPLC purification. A Vydac preparative C-18 reversed-phase column (25×100 mm) was used for purification and a Vydac C-18 analytical column (0.46×25 mm) for purity assessment. In both cases, gradients of acetonitrile (with 0.1% TFA) and water (0.1% TFA) were used for chromatographic fractionation. Elution of peptide elution was monitored at 220 nm and 280 nm. The appropriate HPLC fractions were combined, concentrated by centrifugal evaporation, and lyophilized.

The purity of the final synthetic product was established by HPLC analysis and acid-urea polyacrylamide gel electrophoresis. Molecular mass was determined by MALDI-TOF mass spectrometry, and composition and quantity of peptide were determined by amino acid analysis. Indolicidin analogs synthesized and characterized in the above manner are shown in Tables 1 to 3.

TABLE 1

TRUNCATED INDOLICIDIN ANALOGS

| NAME | AMINO ACID SEQUENCE | SEQ ID NO: |
|---|---|---|
| Indol 1-13* | $H_2$N-I-L-P-W-K-W-P-W-W-P-W-R-R-CON$H_2$ | 1 |
| Indol 2-13 | $H_2$N-L-P-W-K-W-P-W-W-P-W-R-R-CON$H_2$ | 2 |
| Indol 3-13 | $H_2$N-P-W-K-W-P-W-W-P-W-R-R-CON$H_2$ | 3 |
| Indol 4-13 | $H_2$N-W-K-W-P-W-W-P-W-R-R-CON$H_2$ | 4 |
| Indol 5-13 | $H_2$N-K-W-P-W-W-P-W-R-R-CON$H_2$ | 5 |
| Indol 6-13 | $H_2$N-W-P-W-W-P-W-R-R-CON$H_2$ | 6 |
| Indol 7-13 | $H_2$N-P-W-W-P-W-R-R-CON$H_2$ | 7 |
| Indol 8-13 | $H_2$N-W-W-P-W-R-R-CON$H_2$ | 8 |
| Indol 9-13 | $H_2$N-W-P-W-R-R-CON$H_2$ | 9 |

*indolicidin (naturally occurring)

TABLE 2

INDOLICIDIN INDOL (TRP/PHE) ("INDOL/F") ANALOGS

| NAME | AMINO ACID SEQUENCE | SEQ ID NO: |
|---|---|---|
| Indol 1-13* | $H_2$N-I-L-P-W-K-W-P-W-W-P-W-R-R-CON$H_2$ | 1 |
| Indol 1-13/F | $H_2$N-I-L-P-F-K-F-P-F-F-P-F-R-R-CON$H_2$ | 10 |
| Indol 2-13/F | $H_2$N-L-P-F-K-F-P-F-F-P-F-R-R-CON$H_2$ | 11 |
| Indol 3-13/F | $H_2$N-P-F-K-F-P-F-F-P-F-R-R-CON$H_2$ | 12 |
| Indol 4-13/F | $H_2$N-F-K-F-P-F-F-P-F-R-R-CON$H_2$ | 13 |
| Indol 5-13/F | $H_2$N-K-F-P-F-F-P-F-R-R-CON$H_2$ | 14 |
| Indol 6-13/F | $H_2$N-F-P-F-F-P-F-R-R-CON$H_2$ | 15 |
| Indol 7-13/F | $H_2$N-P-F-F-P-F-R-R-CON$H_2$ | 16 |
| Indol 8-13/F | $H_2$N-F-F-P-F-R-R-CON$H_2$ | 17 |
| Indol 9-13/F | $H_2$N-F-P-F-R-R-CON$H_2$ | 18 |

*indolicidin (naturally occurring)

TABLE 3

INDOLICIDIN AMINO AND CARBOXY TERMINAL TRUNCATED ANALOGS

| NAME | AMINO ACID SEQUENCE | SEQ ID NO: |
|---|---|---|
| Indol 1-13* | $H_2$N-I-L-P-W-K-W-P-W-W-P-W-R-R-CON$H_2$ | 1 |
| Indol 1-12 | $H_2$N-I-L-P-W-K-W-P-W-W-P-W-R-CON$H_2$ | 25 |
| Indol 2-12 | $H_2$N-L-P-W-K-W-P-W-W-P-W-R-CON$H_2$ | 26 |
| Indol 3-12 | $H_2$N-P-W-K-W-P-W-W-P-W-R-CON$H_2$ | 27 |
| Indol 4-12 | $H_2$N-W-K-W-P-W-W-P-W-R-CON$H_2$ | 28 |
| Indol 5-12 | $H_2$N-K-W-P-W-W-P-W-R-CON$H_2$ | 29 |
| Indol 6-12 | $H_2$N-W-P-W-W-P-W-R-CON$H_2$ | 30 |
| Indol 1-11 | $H_2$N-I-L-P-W-K-W-P-W-W-P-CON$H_2$ | 31 |
| Indol 2-11 | $H_2$N-L-P-W-L-W-P-W-W-P-CON$H_2$ | 32 |
| Indol 3-11 | $H_2$N-P-W-K-W-P-W-W-P-CON$H_2$ | 33 |
| Indol 1-10 | $H_2$N-I-L-P-W-K-W-P-W-W-P-CON$H_2$ | 34 |

*indolicidin (naturally occurring)

B. Expression of Indol-Hse Analogs:

Indol-Hse was expressed from a recombinant construct encoding three repeats of the mature peptide, each separated by a hexapeptide spacer sequence; poly-(Indol(1–13)-Met-Ala-Arg-Ile-Ala-Met)$_3$ (see FIG. 6). The recombinant indolicidin was produced as a fusion polypeptide with a maltose-binding protein (MBP) and recovered by cleavage with cyanogen bromide.

The multicopy indolicidin encoding DNA sequence was assembled from six synthetic oligonucleotides (see FIG. 6). The oligonucleotides were phosphorylated and assembled by annealing and ligation each fragment (Ikehara et al., Proc. Natl. Acad. Sci., USA 81:2956–5960 (1984), which is incorporated herein by reference). The oligonucleotides (2.5 nmol each) were phosphorylated by treatment with 10 mmol ATP at pH 8.0, heated for 2 min in boiling water, then 9.5 units of polynucleotide kinase was added and the samples were incubated at 37° C. for 120 min. The reaction was stopped by incubating the samples for 15 min at 70° C. Phosphorylated fragments and nonphosphorylated ends were mixed, heated for 2 min in boiling water, and the annealing of the pairs was completed after slow cooling to 15° C. and incubation over night. The samples were phenol/chloroform purified and EtOH precipitated. The annealed DNA mixtures were mixed together and treated with T4 ligase 1.2 units for 15 hr at 15° C. The mixture was heated for 2 min at 70° C. to inactivate the ligase.

A 211 base pair (bp) ligation product was isolated from an agarose gel following electrophoresis using the WIZARD PCR purification kit (Promega; Madison Wis.); PCR was performed using the primers as shown in FIG. 6 (double underlined sequence). The purified 211 bp PCR product was digested with Sal I and Eco RI, then ligated into the Sal I and Eco RI sites of precut pMAL-c2 vector (New England BioLabs; Beverly Mass.). Transformation of INVαF' E. coli was carried out with the TA cloning kit as per the manufacturers directions (Invitrogen; La Jolla Calif.). The DNA sequence shown in FIG. 6 was confirmed by dideoxy sequencing.

The INVαF' cells containing the poly-indolicidin analog pMAL-c2 fusion polypeptide were grown overnight in 15 ml LB media containing 100 μg/ml ampicillin at 37° C. with constant shaking. Ten ml of the overnight culture was transferred into 1 liter of fresh LB/ampicillin media containing 0.2% glucose and incubated with constant shaking for 4 hr to an $OD_{620}$=0.500. IPTG was added to a final concentration of 0.3 mM and the culture was incubated for an additional 4 hr, then the cells were harvested by centrifugation at 4° C.

The cell pellet was suspended in 20 ml ice cold lysis buffer (0.01 M Tris-HCl, pH 8.0; 1 mM each of PMSF, DTT and EDTA; 2 mg/ml lysozyme), then mixed slowly for 30 min on ice. 1.6 ml of 10% sodium deoxycholate and 63 μl of a 2 mg/ml solution of DNAse I were added and the mixture was incubated for an additional 30 min on ice. 3.2 ml of 2% protamine sulfate was added and the mixture was mixed for 20 min on ice. Soluble fusion polypeptide was obtained in the supernatant after centrifugation for 30 min 12,000 rpm. The fusion polypeptide was purified using an amylose affinity resin (New England BioLabs).

The lysis supernatant was diluted 10 to 25-fold with column buffer (0.2 M NaCl; 0.02 M Tris-HCl pH 8.0; 1 mM each DTT and EDTA) before applying to the column. From 2 liters of bacterial culture, approximately 80 mg of maltose binding protein (MBP)-indolicidin fusion polypeptide was purified by amylose affinity chromatography. The purified fusion polypeptide (80 mg) was dialyzed against 1% acetic acid, lyophilized, and dissolved in 4 ml of 80% formic acid containing 160 mg CNBr. The solution was purged with nitrogen, and incubated at room temperature for 5 hr. The solution was diluted 10 fold with water, lyophilized, then the digest was purified by RP-HPLC. The recovery of Indol (1–13)-Hse was approximately 50% of the theoretical yield.

Alternatively, an MBP-indolicidin fusion polypeptide as in FIG. 6 can be prepared, except having the sequence Met-Ala-Arg-Ile-Ala-Met (SEQ ID NO: 21) in place of the Met residue shown between the enterokinase cleavage site and the first CNBr cleavage site (see FIG. 6). Such an MBP-indolicidin fusion polypeptide can be cleaved first with enterokinase, to release the MBP portion of the fusion polypeptide. The poly-indolicidin portion then can be treated with CNBr, to release the Indol-Hse analogs, which can be purified as above.

The results discussed above indicate that poly-indolicidin analog polypeptides can be produced in vivo in a bacterial expression system, without killing the host microorganism, and, therefore, provides a means to produce substantial amounts of Indol-Hse analogs.

EXAMPLE II

Antimicrobial Activity of Indolicidin Analogs

This example demonstrates that various indolicidin analogs of the invention exhibit broad spectrum antimicrobial activity.

The antimicrobial activity of the indolicidin analogs was determined using microbicidal or microbial inhibition assays. The indolicidin analogs initially were characterized using a microbial inhibition method, including a modified plate diffusion assay (Hultmark et al., *EMBO J.* 2:571–573 (1983); Lehrer et al., *J. Immunol. Meth.* 137:167–173 (1991), each of which is incorporated herein by reference).

Nutrient-containing agar (or agarose) plates were seeded with a selected target microorganism and peptide samples (5–10 μl) were placed into small wells formed in the solid medium. Following an initial incubation interval of 1 to 4 hr, the well-containing layer was overlayed with enriched (2× normal) solid medium in order to support microbial growth outside the perimeter of inhibition. After overnight incubation at 30° C. to 37° C., the antimicrobial activity was quantitated by measuring the clear zones around each well (zone of inhibition).

Microbicidal activity was measured by first incubating the target organism with an indolicidin analog in an aqueous suspension, then plating the suspension to quantitate surviving microorganisms. Cultures were grown to mid log phase in an appropriate medium, harvested, washed, and resuspended to $1–2 \times 10^7$ colony forming units (CFU) per ml. To conserve peptide, the incubation volume usually was 0.05 ml, with the final cell concentration being $1–2 \times 10^6$ CFU/ml. Peptide stock solutions, usually made up in 0.01% acetic acid, were diluted in the incubation buffer to a final concentration of 1 μg/ml to 100 μg/ml, and the incubation was initiated by addition of an appropriate volume of the bacterial or fungal stock suspension to the prewarmed (37° C.) peptide-buffer mixture. At timed intervals, 50 μl or 100 μl samples were removed and diluted serially, then plated on nutrient-containing agar plates. Killing activity was quantitated by determining the reduction in CFU relative to appropriate control incubations.

Indolicidin analogs lacking up to 5 amino terminal amino acids were as effective as synthetic Indol 1–13 (SEQ ID NO: 1) in inhibiting the growth of *E. coli* and *S. aureus* (FIGS. 1A and 1B). Further amino terminal deletion reduced the antimicrobial activity of the analogs, although activity was maintained at the highest doses examined. In comparison, substantial activity against fungi, including *C. neoformans* and *C. albicans* was maintained by indolicidin analogs lacking as many as seven amino terminal amino acids (FIGS. 1C and 1D).

Similar results were obtained when the amino terminal truncated indolicidin analogs were examined in a suspension assay to determine the killing activity of the peptides. The killing activity of the peptides against *E. coli* and *S. aureus* was similar to the results obtained for the agar diffusion assay (compare FIGS. 2A and 2B with FIGS. 1A and 1B). In addition, the indolicidin analogs were particularly effective in killing *C. neoformans* (FIG. 2C), although there was less killing activity by the shorter peptides against *C. albi-* cans (FIG. 2D). These results indicate that amino terminal truncated indolicidin analogs have antimicrobial activity that is equivalent to that of naturally occurring indolicidin.

Figure 7:
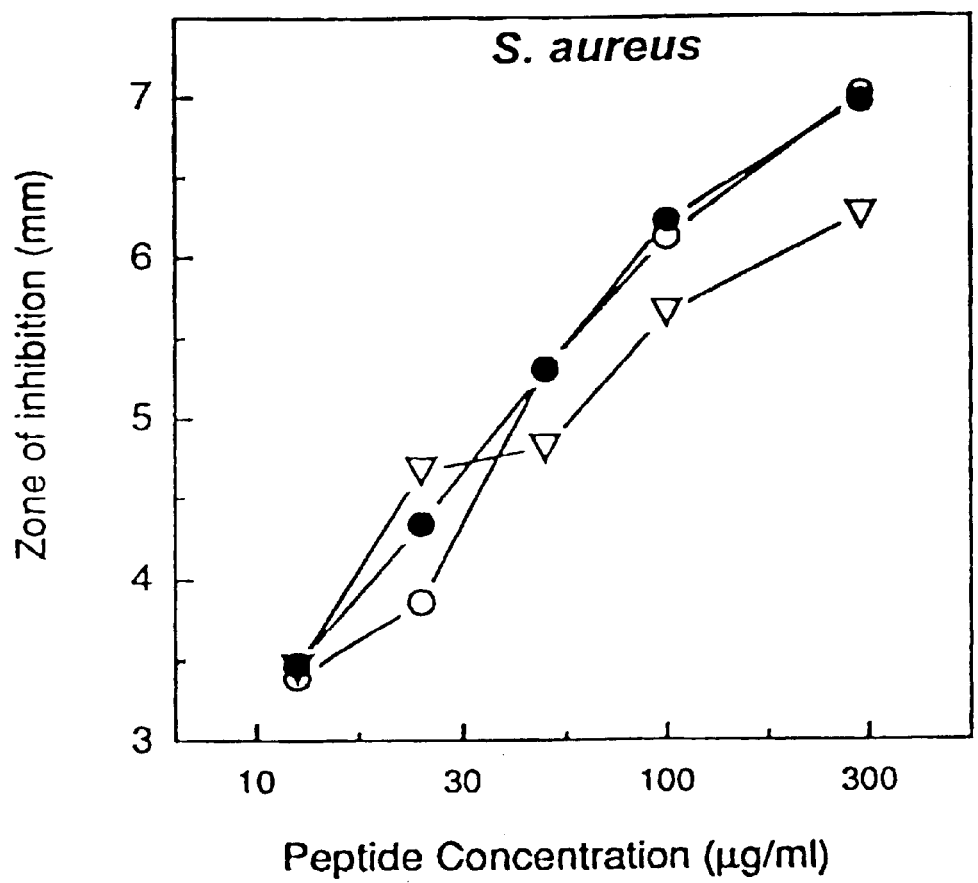
FIG. 7 compares the antimicrobial activity of Indol 1–13 (SEQ ID NO: 1; open circles), synthetic Indol(1–13)-Hse (diamonds) and Indol(1–13)-Hse derived from poly-(Indol (1–13)-Met-Ala-Arg-Ile-Ala-Met)$_3$ (closed circles; see FIG. 6) using an agar diffusion assay. Peptides were examined at various concentrations, as indicated. against *S. aureus* and zones of inhibition were determined (mm).

The antimicrobial activity of Indol-Hse analogs also was examined. Indol-Hse analogs were produced by cyanogen bromide cleavage of Indol(1–13)-Met-Gly-Ser-Glu (SEQ ID NO: 35), followed by isolation of the carboxylic acid form from the lactone form, which otherwise exist in equilibrium. As shown in FIGS. 3A and 3B, both forms of the Indol-Hse analog have antimicrobial activity equivalent to Indol 1–13 (SEQ ID NO: 1) against *S. aureus* and *E. coli*, as well as the ability to kill *E. coli* (FIG. 3C). Indol(1–13)-Hse prepared from a poly-indolicidin polypeptide expressed recombinantly also had antimicrobial activity equivalent to that of synthesized Indol 1–13 (SEQ ID NO: 1) and synthesized Indol(1–13)-Hse (FIG. 7).

Amino terminal truncated Indol-Hse analogs also were examined for antimicrobial activity. Indol-Hse analogs lacking as many as 5 amino terminal amino acids had antimicrobial activity against *S. aureus* and *E. coli* (FIG. 4), although the activity began decreasing in the Indol(6–13)-Hse analog as compared to the Indol(5–13)-Hse analog (see FIGS. 4C and 4F). These results demonstrate that Indol-Hse analogs, including amino terminal truncated analogs, exhibit antimicrobial activity equivalent to that of naturally occurring Indol 1–13 (SEQ ID NO: 1).

Figure 5:
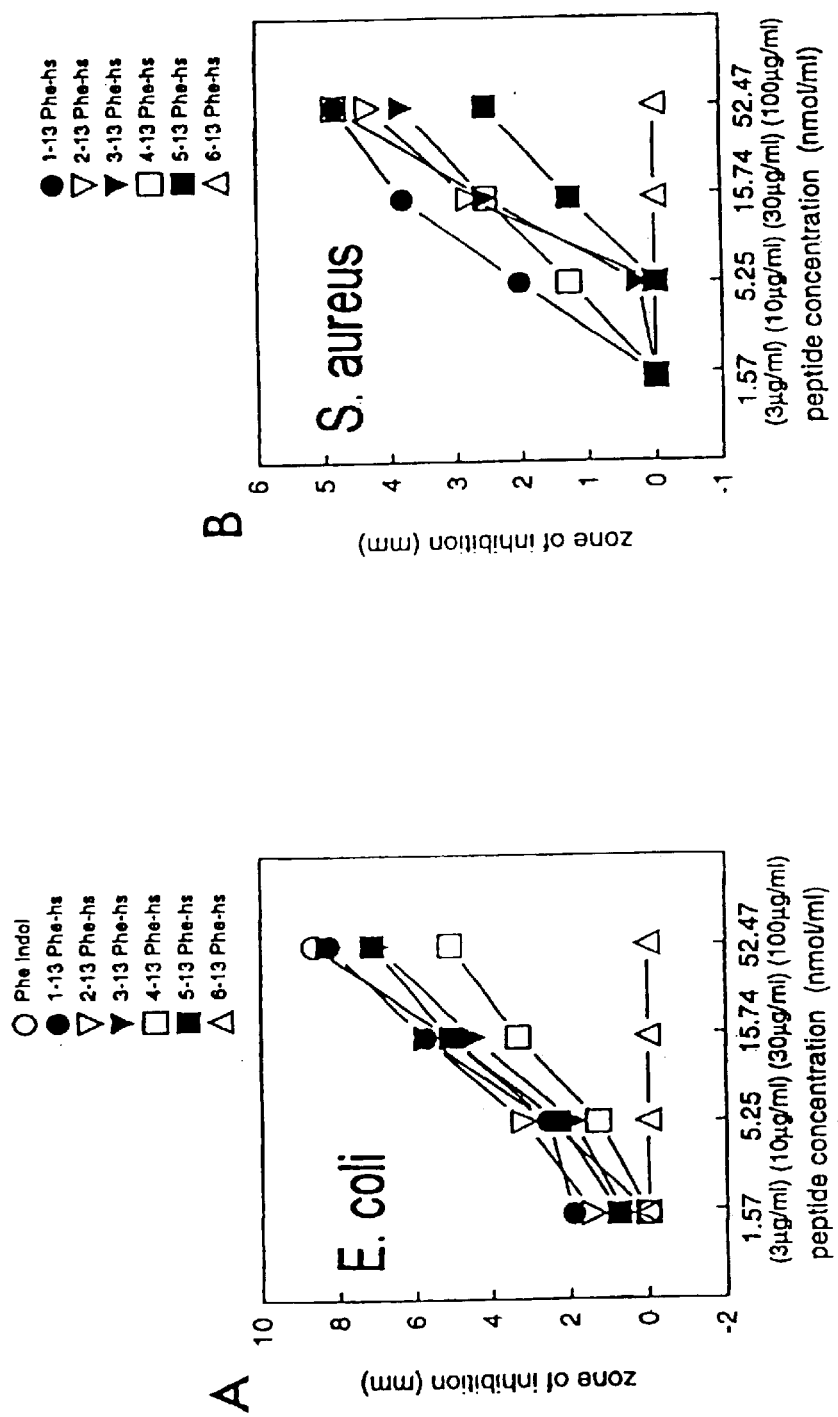
FIG. 5A and 5B compare the antimicrobial activities of Indol(1–13)-Hse/Phe analogs, in which all Trp residues of Indol 1–13 (SEQ ID NO: 1) are replaced by Phe residues and each peptide contains a carboxy terminal homoserine (Hse) residue, using an agar diffusion assay. Peptides were tested at concentrations ranging from 1.57 µM to 52.5 µM against *E. coli* (FIG. 5A) or *S. aureus* (FIG. 5B).

The antimicrobial activity of Indol/F-Hse analogs against *E. coli* and *S. aureus* also was examined. As shown in FIG. 5, amino terminal truncated Indol/F-Hse analogs lacking as many as 4 amino terminal amino acid residues had antimicrobial activity equivalent to that of Indol(1–13)/F. These results indicate that Trp in naturally occurring indolicidin can be substituted with Phe without destroying the antimicrobial activity of the peptide.

Although the invention has been described with reference to the examples provided above, it should be understood that various modifications can be made without departing from the spirit of the invention. Accordingly, the invention is limited only by the claims.

What is claimed is:

1. An isolated nucleic acid molecule encoding an indolicidin analog having the amino acid sequence:

Xaa1-Xaa2-Xaa3-Xaa4-Xaa5-Xaa6-Pro-Xaa6-Xaa6-Pro-Xaa6-Pro-Xaa7-Xaa7-Xaa8, wherein:

Xaa1 is Ile, Leu, Val, Ala, Gly or absent;
Xaa2 is Ile, Leu, Val, Ala, Gly or absent;
Xaa3 is Pro or absent;
Xaa4 is Trp, Phe or absent;
Xaa5 is Arg, Lys or absent;
Xaa6 is Trp or Phe;
Xaa7 is Arg, Lys or absent; and
Xaa8 is Met-Xaa9-Met;
wherein Xaa9 is at least one amino acid;
and further provided that
if Xaa2 is absent, Xaa1 is absent;
if Xaa3 is absent, Xaa1 and Xaa2 are absent;
if Xaa4 is absent, Xaa1, Xaa2 and Xaa3 are absent; and
if Xaa5 is absent, Xaa1, Xaa2, Xaa3 and Xaa4 are absent.

2. An isolated nucleic acid molecule encoding an indolicidin analog having the amino acid sequence selected from the group consisting of:

H$_2$N-Leu-Pro-Phe-Lys-Phe-Pro-Phe-Phe-Pro-Phe-Arg-Arg-CONH$_2$ (SEQ ID NO:11);
H$_2$N-Pro-Phe-Lys-Phe-Pro-Phe-Phe-Pro-Phe-Arg-Arg-CONH$_2$ (SEQ ID NO: 12);
H$_2$N-Phe-Lys-Phe-Pro-Phe-Phe-Pro-Phe-Arg-Arg-CONH$_2$ (SEQ ID NO: 13);
H2N-Ile-Leu-Pro-Trp-Lys-Trp-Pro-Trp-Trp-Pro-Trp-Arg-Arg-Met (SEQ ID NO: 36); and
H$_b$ $_2$N-Ile-Leu-Pro-Trp-Lys-Trp-Pro-Trp-Trp-Pro-Trp-Arg-Arg-Met-Xaa9-Met (SEQ ID NO: 37), wherein Xaa9 is at least one amino acid, said encoded indolicidin having antimicrobial activity.

3. An isolated nucleic acid molecule encoding an indolicidin consisting of the amino acid sequence:

Xaa1-Xaa2-Xaa3-Xaa4-Xaa5-Xaa6-Pro-Xaa6-Xaa6-Pro-Xaa6-Xaa7-Xaa7-Xaa8, wherein:

Xaa1 is Ile, Leu, Val, Ala, Gly or absent;
Xaa2 is Ile, Leu, Val, Ala, Gly or absent;
Xaa3 is Pro or absent;
Xaa4 is Trp, Phe or absent;
Xaa5 is Arg, Lys or absent;
Xaa6 is Trp or Phe;
Xaa7 is Arg, Lys or absent; and
Xaa8 is Me or Met-Xaa9-Met;
wherein Xaa9 is at least one amino acid;
and further provided that
if Xaa2 is absent, Xaa1 is absent;
if Xaa3 is absent, Xaa1 and Xaa2 are absent;
if Xaa4 is absent, Xaa1, Xaa2 and Xaa3 are absent; and
if Xaa5 is absent, Xaa1, Xaa2, Xaa3 and Xaa4 are absent.

4. The nucleic acid of claim 3, wherein Xaa8 is Met.

5. The nucleic acid of claim 3, wherein Xaa8 is Met-Xaa9-Met.

6. The nucleic acid molecule of claim 2, said indolicidin analog having the amino acid sequence is H$_2$N-Leu-Pro-Phe-Lys-Phe-Pro-Phe-Phe-Pro-Phe-Arg-Arg-CONH$_2$ (SEQ ID NO:11).

7. The nucleic acid molecule of claim 1, said indolicidin analog consisting of the amino acid sequence H$_2$N-Leu-Pro-Phe-Lys-Pre-Pho-Phe-Pre-Pro-Phe-Arg-Arg-CONH$_2$ (SEQ ID NO:11).

8. The nucleic acid molecule of claim 2, said indolicidin analog having the amino acid sequence H$_2$N-Pro-Phe-Lys-Phe-Pro-Phe-Phe-Pro-Phe-Arg-Arg-CONH$_2$ (SEQ ID NO: 12).

9. The nucleic acid molecule of claim 1, said indolicidin analog consisting of the amino acid sequence H$_2$N-Pro-Phe-Lys-Phe-Pro-Phe-Phe-Pro-Phe-Arg-Arg-CONH$_2$ (SEQ ID NO: 12).

10. The nucleic acid molecule claim 2, said indolicidin analog having the amino acid sequence H$_2$N-Phe-Lys-Phe-Pro-Phe-Phe-Pro-Phe-Arg-Arg-CONH$_2$ (SEQ ID NO: 13).

11. The nucleic acid molecule of claim 1, said indolicidin analog consisting of the amino acid sequence H$_2$N-Phe-Lys-Phe-Pro-Phe-Phe-Pro-Phe-Arg-Arg-CONH$_2$ (SEQ ID NO: 13).

12. The nucleic acid molecule of claim 2, said indolicidin analog having the amino acid sequence H$_2$N-Ile-Leu-Pro-Trp-Lys-Trp-Pro-Trp-Trp-Pro-Trp-Arg-Arg-Met (SEQ ID NO: 36).

13. The nucleic acid molecule of claim 1, said indolicidin analog consisting of the amino acid sequence H$_2$N-Ile-Leu-Pro-Trp-Lys-Trp-Pro-Trp-Trp-Pro-Trp-Arg-Arg-Met (SEQ ID NO: 36).

14. The nucleic acid molecule of claim 2, said indolicidin analog having the amino acid sequence H₂N-Ile-Leu-Pro-Trp-Lys-Trp-Pro-Trp-Trp-Pro-Trp-Arg-Arg-Met-Xaa9-Met (SEQ ID NO: 37), wherein Xaa9 is at least one amino acid.

15. The nucleic acid molecule of claim 1, said indolicidin analog consisting of the amino acid sequence H₂-Ile-Leu-Pro-Trp-Lys-Trp-Pro-Trp-Trp-Pro-Trp-Arg-Arg-Met-Xaa9-Met (SEQ ID NO: 37), wherein Xaa9 is at least one amino acid.

16. An isolated nucleic acid molecule encoding an indolicidin analog consisting of the amino acid sequence selected from the group consisting of:

H₂N-Leu-Pro-Trp-Lys-Trp-Pro-Trp-Trp-Pro-Trp-Arg-Arg-CONH₂ (SEQ IDNO:2);

H₂N-Trp-Lys-Trp-Pro-Trp-Trp-Pro-Trp-Arg-Arg-CONH₂ (SEQ ID NO: 4);

H₂N-Leu-Pro-Phe-Lys-Phe-Pro-Phe-Phe-Pro-Phe-Arg-Arg-CONH₂ (SEQ ID NO:11);

H₂N-Pro-Phe-Lys-Phe-Pro-Phe-Phe-Pro-Phe-Arg-Arg-CONH₂ (SEQ ID NO: 12);

H₂N-Phe-Lys-Phe-Pro-Phe-Phe-Pro-Phe-Arg-Arg-CONH₂ (SEQ ID NO: 13);

H₂N-Pro-Trp-Lys-Trp-Pro-Trp-Trp-Pro-Trp-Arg-Arg-CONH₂ SEQ ID NO: 27);

H₂N-Trp-Lys-Trp-Pro-Trp-Trp-Pro-Trp-Arg-CONH₂ (SEQ ID NO: 28);

H₂N-Trp-Pro-Trp-Trp-Pro-Arg-Arg-CONH₂ (SEQ ID NO: 30);

H₂N-Ile-Leu-Pro-Trp-Lys-Trp-Pro-Trp-Trp-Pro-Trp-Arg-Arg-Met (SEQ ID NO: 36); and H₂N-Ile-Leu-Pro-Trp-Lys-Trp-Pro-Trp-Trp-Pro-Trp-Arg-Arg-Met-Xaa9-Met (SEQ ID NO: 37), wherein Xaa9 is at least one amino acid, said encoded indolicidin having antimicrobial activity.

17. The isolated nucleic acid molecule of claim 16, said indolicidin analog consisting of the amino acid sequence selected from the group consisting of:

H₂N-Leu-Pro-Phe-Lys-Phe-Pro-Phe-Phe-Pro-Phe-Arg-Arg-CONH₂ (SEQ ID NO:11);

H₂N-Pro-Phe-Lys-Phe-Pro-Phe-Phe-Pro-Phe-Arg-Arg-CONH₂ (SEQ ID NO: 12);

H₂N-Phe-Lys-Phe-Pro-Phe-Phe-Pro-Phe-Arg-Arg-CONH₂ (SEQ ID NO: 13);

H₂N-Ile-Leu-Pro-Trp-Lys-Trp-Pro-Trp-Trp-Pro-Trp-Arg-Arg-Met (SEQ ID NO: 36); and H₂N-Ile-Leu-Pro-Trp-Lys-Trp-Pro-Trp-Trp-Pro-Trp-Arg-Arg-Met-Xaa9-Met (SEQ ID NO: 37), wherein Xaa9 is at least one amino acid, said encoded indolicidin having antimicrobial activity.

18. The isolated nucleic acid molecule of claim 16, said indolicidin analog consisting of the amino acid sequence selected from the group consisting of:

H₂N-Leu-Pro-Trp-Lys-Trp-Pro-Trp-Trp-Pro-Trp-Arg-Arg-CONH₂ (SEQ IDNO:2);

H₂N-Trp-Lys-Trp-Pro-Trp-Trp-Pro-Trp-Arg-Arg-CONH₂ (SEQ ID NO: 4);

H₂N-Pro-Trp-Lys-Trp-Pro-Trp-Trp-Pro-Trp-Arg-CONH₂ (SEQ ID NO: 27);

H₂N-Trp-Lys-Trp-Pro-Trp-Trp-Pro-Trp-Arg-CONH₂ (SEQ ID NO: 28); and

H₂N-Trp-Pro-Trp-Trp-Pro-Trp-Arg-CONH₂ (SEQ ID NO: 30).

19. The nucleic acid molecule of claim 18, said indolicidin analog consisting of the amino acid sequence H₂N-Leu-Pro-Trp-Lys-Trp-Pro-Trp-Trp-Pro-Trp-Arg-Arg-CONH₂ (SEQ IDNO:2).

20. The nucleic acid molecule of claim 18, said indolicidin analog consisting of the amino acid sequence H₂ N-Trp-Lys-Trp-Pro-Trp-Trp-Pro-Trp-Arg-Arg-CONH₂(SEQ ED NO: 4).

21. The nucleic acid molecule of claim 18, said indolicidin analog consisting of the amino acid sequence H₂N-Pro-Trp-Lys-Trp-Pro-Trp-Trp-Pro-Trp-Arg-CONH₂ (SEQ ID NO: 27).

22. The nucleic acid molecule of claim 18, said indolicidin analog consisting of the amino acid sequence H₂N-Trp-Lys-Trp-Pro-Trp-Trp-Pro-Trp-Arg-CONH₂ (SEQ ID NO: 28).

23. The nucleic acid molecule of claim 18, said indolicidin analog consisting of the amino acid sequence H₂N-Trp-Pro-Trp-Trp-Pro-Trp-Arg-CONH₂ (SEQ ID NO: 30).

* * * * *

```
                           SEQUENCE LISTING

<160> NUMBER OF SEQ ID NOS: 39

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (13)
<223> OTHER INFORMATION: AMIDATION

<400> SEQUENCE: 1

Ile Leu Pro Trp Lys Trp Pro Trp Trp Pro Trp Arg Arg
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (12)
<223> OTHER INFORMATION: AMIDATION

<400> SEQUENCE: 2

Leu Pro Trp Lys Trp Pro Trp Trp Pro Trp Arg Arg
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (11)
<223> OTHER INFORMATION: AMIDATION
```

-continued

```
<400> SEQUENCE: 3

Pro Trp Lys Trp Pro Trp Trp Pro Trp Arg Arg
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (10)
<223> OTHER INFORMATION: AMIDATION

<400> SEQUENCE: 4

Trp Lys Trp Pro Trp Trp Pro Trp Arg Arg
 1               5                  10

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (9)
<223> OTHER INFORMATION: AMIDATION

<400> SEQUENCE: 5

Lys Trp Pro Trp Trp Pro Trp Arg Arg
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (8)
<223> OTHER INFORMATION: AMIDATION

<400> SEQUENCE: 6

Trp Pro Trp Trp Pro Trp Arg Arg
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (7)
<223> OTHER INFORMATION: AMIDATION

<400> SEQUENCE: 7

Pro Trp Trp Pro Trp Arg Arg
 1               5
```

```
<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (6)
<223> OTHER INFORMATION: AMIDATION

<400> SEQUENCE: 8

Trp Trp Pro Trp Arg Arg
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (5)
<223> OTHER INFORMATION: AMIDATION

<400> SEQUENCE: 9

Trp Pro Trp Arg Arg
 1               5

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (13)
<223> OTHER INFORMATION: AMIDATION

<400> SEQUENCE: 10

Ile Leu Pro Phe Lys Phe Pro Phe Phe Pro Phe Arg Arg
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (12)
<223> OTHER INFORMATION: AMIDATION

<400> SEQUENCE: 11

Leu Pro Phe Lys Phe Pro Phe Phe Pro Phe Arg Arg
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      construct
```

```
<220> FEATURE:
<221> NAME/KEY: MOD_RES
<222> LOCATION: (11)
<223> OTHER INFORMATION: AMIDATION

<400> SEQUENCE: 12

Pro Phe Lys Phe Pro Phe Phe Pro Phe Arg Arg
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (10)
<223> OTHER INFORMATION: AMIDATION

<400> SEQUENCE: 13

Phe Lys Phe Pro Phe Phe Pro Phe Arg Arg
 1               5                  10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (9)
<223> OTHER INFORMATION: AMIDATION

<400> SEQUENCE: 14

Lys Phe Pro Phe Phe Pro Phe Arg Arg
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (8)
<223> OTHER INFORMATION: AMIDATION

<400> SEQUENCE: 15

Phe Pro Phe Phe Pro Phe Arg Arg
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (7)
<223> OTHER INFORMATION: AMIDATION

<400> SEQUENCE: 16
```

-continued

Pro Phe Phe Pro Phe Arg Arg
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (6)
<223> OTHER INFORMATION: AMIDATION

<400> SEQUENCE: 17

Phe Phe Pro Phe Arg Arg
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (5)
<223> OTHER INFORMATION: AMIDATION

<400> SEQUENCE: 18

Phe Pro Phe Arg Arg
 1               5

<210> SEQ ID NO 19
<211> LENGTH:
<212> TYPE:
<213> ORGANISM:

<400> SEQUENCE: 19

000

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 20

Met Gly Ser Glu Met
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 21

Met Ala Arg Ile Ala Met
 1               5

<210> SEQ ID NO 22

```
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 22

Ile Leu Pro Phe Lys Phe Pro Phe Phe Pro Phe Arg Arg Met Gly Ser
 1               5                  10                  15

Glu Met Ile Leu Pro Phe Lys Phe Pro Phe Phe Pro Phe Arg Arg Met
            20                  25                  30

<210> SEQ ID NO 23
<211> LENGTH: 14
<212> TYPE: PRT
<213> ORGANISM: Artificial Sequence
<220> FEATURE:
<221> NAME/KEY: MOD_RES
<222> LOCATION: (14)
<223> OTHER INFORMATION: Xaa is homoserine (Hse).
<220> FEATURE:
<223> OTHER INFORMATION: Description of Artificial Sequence: Synthetic
      construct

<400> SEQUENCE: 23

Ile Leu Pro Phe Lys Phe Pro Phe Phe Pro Phe Arg Arg Xaa
 1               5                  10

<210> SEQ ID NO 24
<211> LENGTH: 14
<212> TYPE: PRT
<213> ORGANISM: Artificial Sequence
<220> FEATURE:
<221> NAME/KEY: MOD_RES
<222> LOCATION: (14)
<223> OTHER INFORMATION: Xaa is homoserine (Hse).
<220> FEATURE:
<223> OTHER INFORMATION: Description of Artificial Sequence: Synthetic
      construct

<400> SEQUENCE: 24

Ile Leu Pro Trp Lys Trp Pro Trp Trp Pro Trp Arg Arg Xaa
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (12)
<223> OTHER INFORMATION: AMIDATION

<400> SEQUENCE: 25

Ile Leu Pro Trp Lys Trp Pro Trp Trp Pro Trp Arg
 1               5                  10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
```

```
<222> LOCATION: (11)
<223> OTHER INFORMATION: AMIDATION

<400> SEQUENCE: 26

Leu Pro Trp Lys Trp Pro Trp Trp Pro Trp Arg
 1               5                  10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (10)
<223> OTHER INFORMATION: AMIDATION

<400> SEQUENCE: 27

Pro Trp Lys Trp Pro Trp Trp Pro Trp Arg
 1               5                  10

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (9)
<223> OTHER INFORMATION: AMIDATION

<400> SEQUENCE: 28

Trp Lys Trp Pro Trp Trp Pro Trp Arg
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (8)
<223> OTHER INFORMATION: AMIDATION

<400> SEQUENCE: 29

Lys Trp Pro Trp Trp Pro Trp Arg
 1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (7)
<223> OTHER INFORMATION: AMIDATION

<400> SEQUENCE: 30

Trp Pro Trp Trp Pro Trp Arg
 1               5
```

```
<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (11)
<223> OTHER INFORMATION: AMIDATION

<400> SEQUENCE: 31

Ile Leu Pro Trp Lys Trp Pro Trp Trp Pro Trp
 1               5                  10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (10)
<223> OTHER INFORMATION: AMIDATION

<400> SEQUENCE: 32

Leu Pro Trp Leu Trp Pro Trp Trp Pro Trp
 1               5                  10

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (9)
<223> OTHER INFORMATION: AMIDATION

<400> SEQUENCE: 33

Pro Trp Lys Trp Pro Trp Trp Pro Trp
 1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (10)
<223> OTHER INFORMATION: AMIDATION

<400> SEQUENCE: 34

Ile Leu Pro Trp Lys Trp Pro Trp Trp Pro
 1               5                  10

<210> SEQ ID NO 35
<211> LENGTH: 17
<212> TYPE: PRT
<213> ORGANISM: Artificial Sequence
<220> FEATURE:
```

<223> OTHER INFORMATION: Description of Artificial Sequence: Synthetic
      construct

<400> SEQUENCE: 35

Ile Leu Pro Trp Lys Trp Pro Trp Trp Pro Trp Arg Arg Met Gly Ser
 1               5                  10                  15

Glu

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 36

Ile Leu Pro Trp Lys Trp Pro Trp Trp Pro Trp Arg Arg Met
 1               5                  10

<210> SEQ ID NO 37
<211> LENGTH: 16
<212> TYPE: PRT
<213> ORGANISM: Artificial Sequence
<220> FEATURE:
<221> NAME/KEY: SITE
<222> LOCATION: (14)
<223> OTHER INFORMATION: Xaa is at least one amino acid
<220> FEATURE:
<223> OTHER INFORMATION: Description of Artificial Sequence: Synthetic
      construct

<400> SEQUENCE: 37

Ile Leu Pro Trp Lys Trp Pro Trp Trp Pro Trp Arg Arg Met Xaa Met
 1               5                  10                  15

<210> SEQ ID NO 38
<211> LENGTH: 211
<212> TYPE: DNA
<213> ORGANISM: Artificial Sequence
<220> FEATURE:
<221> NAME/KEY: CDS
<222> LOCATION: (8)..(196)
<220> FEATURE:
<223> OTHER INFORMATION: Description of Artificial Sequence: Synthetic
      construct

<400> SEQUENCE: 38 ggaattc gac gac gac gac aaa atg atc ctg ccg tgg aaa tgg ccg tgg        49
        Asp Asp Asp Asp Lys Met Ile Leu Pro Trp Lys Trp Pro Trp
         1               5                  10 tgg ccg tgg cgt cgt atg gct cgt atc gct atg atc ctg ccg tgg aaa        97
Trp Pro Trp Arg Arg Met Ala Arg Ile Ala Met Ile Leu Pro Trp Lys
 15                  20                  25                  30 tgg ccg tgg tgg ccg tgg cgt cgt atg gct cgt atc gct atg atc ctg       145
Trp Pro Trp Trp Pro Trp Arg Arg Met Ala Arg Ile Ala Met Ile Leu
                 35                  40                  45 ccg tgg aaa tgg ccg tgg tgg ccg tgg cgt cgt atg gct cgt atc gct       193
Pro Trp Lys Trp Pro Trp Trp Pro Trp Arg Arg Met Ala Arg Ile Ala
             50                  55                  60 atg taataagtcg accgg                                                   211
Met

<210> SEQ ID NO 39
<211> LENGTH: 63
<212> TYPE: PRT

-continued

```
<213> ORGANISM: Artificial Sequence
<220> FEATURE:
<223> OTHER INFORMATION: Description of Artificial Sequence: Synthetic
      construct

<400> SEQUENCE: 39

Asp Asp Asp Asp Lys Met Ile Leu Pro Trp Lys Trp Pro Trp Trp Pro
 1               5                  10                  15

Trp Arg Arg Met Ala Arg Ile Ala Met Ile Leu Pro Trp Lys Trp Pro
                20                  25                  30

Trp Trp Pro Trp Arg Arg Met Ala Arg Ile Ala Met Ile Leu Pro Trp
            35                  40                  45

Lys Trp Pro Trp Trp Pro Trp Arg Arg Met Ala Arg Ile Ala Met
 50                  55                  60
```